United States Patent
Hayashi et al.

(10) Patent No.: US 8,801,180 B2
(45) Date of Patent: Aug. 12, 2014

(54) OPHTHALMIC TOMOGRAPHIC IMAGER WITH CORNEO-RETINAL IMAGE ANALYSIS

(75) Inventors: Takefumi Hayashi, Tokyo (JP); Hitoshi Shimizu, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 269 days.

(21) Appl. No.: 12/996,935

(22) PCT Filed: Jun. 8, 2009

(86) PCT No.: PCT/JP2009/002565
§ 371 (c)(1),
(2), (4) Date: Dec. 8, 2010

(87) PCT Pub. No.: WO2009/153929
PCT Pub. Date: Dec. 23, 2009

(65) Prior Publication Data
US 2011/0080561 A1    Apr. 7, 2011

(30) Foreign Application Priority Data
Jun. 19, 2008   (JP) ................................ 2008-160548

(51) Int. Cl.
*A61B 3/10* (2006.01)
*G01B 9/02* (2006.01)
*G01B 11/24* (2006.01)

(52) U.S. Cl.
CPC ............ *A61B 3/1005* (2013.01); *G01B 11/2441* (2013.01); *A61B 3/102* (2013.01); *G01B 9/02091* (2013.01); *G01B 9/02028* (2013.01); *G01B 9/02085* (2013.01)
USPC ...................................................... 351/206

(58) Field of Classification Search
CPC .............................. A61B 3/102; A61B 3/1005
USPC .......................................... 351/205, 206, 246
See application file for complete search history.

(56) References Cited

U.S. PATENT DOCUMENTS 6,198,540 B1   3/2001   Ueda et al.
6,377,349 B1   4/2002   Fercher
(Continued)

FOREIGN PATENT DOCUMENTS

JP   09-276232 A   10/1997
JP   10-267830 A   10/1998
(Continued)

OTHER PUBLICATIONS

Sekine, Akihiko et al.. "Axial Eye-length Measurement by Wavelength-shift Interferometry." Journal of the Optical Society of America 10.7 (1993): 1651-1655.*

(Continued)

*Primary Examiner* — Zachary Wilkes
(74) *Attorney, Agent, or Firm* — Pearne & Gordon LLP

(57) ABSTRACT

An optical image measuring device 1 splits low-coherence light L0 into signal light LS and reference light LR, and splits an optical path of the reference light LR into two optical paths having different optical path lengths to split the reference light LR into two reference lights LRa, LRb. Furthermore, the optical image measuring device 1 makes the reference lights LRa, LRb interfere with the signal light LS propagated through an eye E, generates an interference light LC reflecting a morphology in each of two depth positions (fundus oculi Ef and cornea Ec) of an eye E, and detects the interference light LC to generate a detection signal. Then, the optical image measuring device 1 forms a fundus oculi tomographic image and a cornea tomographic image based on the detection signals, and analyzes the tomographic images to obtain a distance between the cornea and retina of the eye E.

15 Claims, 9 Drawing Sheets

(56) References Cited

U.S. PATENT DOCUMENTS

| | | |
|---|---|---|
| 7,345,770 B2 | 3/2008 | Chan et al. |
| 7,400,410 B2 * | 7/2008 | Baker et al. .................. 351/210 |
| 2005/0219544 A1 * | 10/2005 | Chan et al. .................. 356/497 |
| 2007/0076217 A1 | 4/2007 | Baker et al. |
| 2008/0285043 A1 | 11/2008 | Fercher et al. |

FOREIGN PATENT DOCUMENTS

| | | |
|---|---|---|
| JP | 11-325849 A | 11/1999 |
| JP | 2002-139421 A | 5/2002 |
| JP | 2006-153838 A | 6/2006 |
| JP | 2007-024677 A | 2/2007 |
| JP | EP1780530 A1 | 5/2007 |
| JP | 2008-073099 A | 4/2008 |
| WO | 2007/065670 A2 | 6/2007 |

OTHER PUBLICATIONS

Felipe, Adelina, et al. "Optical Analysis to Predict Outcomes after Implantation of a Double Intraocular Lens Magnification Device." J. Cataract Refract. Surgery 33 (2007): 1781-1789.*
International Search Report for PCT/JP2009/00265; Jul. 7, 2009.
Extended European Search Report for 09766377.7-1660/2301423 dated Mar. 7, 2013.

* cited by examiner

OPHTHALMIC TOMOGRAPHIC IMAGER WITH CORNEO-RETINAL IMAGE ANALYSIS

TECHNICAL FIELD

The present invention relates to an optical image measuring device configured to form images that show the surface morphology and internal morphology of measured objects by using a light beam.

BACKGROUND ART

In recent years, an optical image measuring technique of forming images that show the surface morphology and internal morphology of measured objects by using a light beam from a laser light source or the like has attracted attention. Unlike an X-ray CT apparatus, the optical image measuring technique is noninvasive to human bodies, and is therefore expected to be utilized more particularly in the medical field and biological field.

Patent Document 1 discloses a device to which the optical image measuring technique is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT (Optical Coherence Tomography)." That is to say, the device radiates a low-coherence light beam to a measured object, superposes the reflected light and the reference light to generate an interference light, and acquires the spectral intensity distribution of the interference light to execute Fourier transform, thereby imaging the morphology in the depth direction (the z-direction) of the measured object.

Furthermore, the device described in Patent Document 1 is provided with a Galvano mirror that scans with a light beam (a signal light), and is thereby configured to form an image of a desired measurement target region of the measured object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction and the vertical direction to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of optical image measuring devices. Patent Document 3 describes an optical image measuring device that images the morphology of a measured object by scanning the measured object with light of various wavelengths, acquiring the spectral intensity distribution based on an interference light obtained by superposing the reflected lights of the light of the respective wavelengths on the reference light, and executing Fourier transform. Such an optical image measuring device is called a Swept Source type or the like.

Further, Patent Document 4 describes an optical image measuring device that radiates a light having a predetermined beam diameter to a measured object and analyzes the components of an interference light obtained by superposing the reflected light and the reference light, thereby forming an image of the measured object in a cross-section orthogonal to the travelling direction of the light. Such an optical image measuring device is called a full-field type, en-face type or the like.

Patent Document 5 discloses a configuration in which the OCT technique is applied to the ophthalmologic field. Before the optical image measuring device was applied to the ophthalmologic field, a fundus oculi observing device such as a retinal camera had been used (for example, refer to Patent Document 6).

A fundus oculi imaging device using the OCT technique has a merit that a tomographic image and three-dimensional image of the fundus oculi can be acquired, as compared with a retinal camera that merely images the fundus oculi surface from the front. Therefore, contribution to increase of the diagnosis accuracy and early detection of a lesion is expected.

Patent Document 1: Japanese Unexamined Patent Application Publication No. 11-325849
Patent Document 2: Japanese Unexamined Patent Application Publication No. 2002-139421
Patent Document 3: Japanese Unexamined Patent Application Publication No. 2007-24677
Patent Document 4: Japanese Unexamined Patent Application Publication No. 2006-153838
Patent Document 5: Japanese Unexamined Patent Application Publication No. 2008-73099
Patent Document 6: Japanese Unexamined Patent Application Publication No. 9-276232

DISCLOSURE OF THE INVENTION

Problem that the Invention is to Solve

An image acquired by an optical image measuring device (an OCT image: a tomographic image, a three-dimensional image, and so on) is used for measurement of various physical quantities of (part of) a measured object. For example, in the ophthalmologic field, this image is utilized for measurement of physical quantities such as the size of a lesion site and a chamber angle.

However, with a conventional optical image measuring device, it is possible to measure the physical quantity of an object depicted in one OCT image, but it is difficult to measure, with high accuracy, the physical quantity of an object depicted in a plurality of OCT images.

For example, with a conventional optical image measuring device, it was possible to measure a distance between two points in one OCT image, but it was difficult to measure a distance between one point in a first OCT image and one point in a second OCT image with high accuracy. Particularly in the case of a measured object such as a living eye, which is not in a still condition, a gap in acquisition timing was made between the first OCT image and the second OCT image, and consequently, it was quite possible that the accuracy of measurement decreases.

Thus, with a conventional optical image measuring device, it was easy to measure a physical quantity in a relatively narrow range that can be depicted in one OCT image, but it was difficult to measure, with high accuracy, a physical quantity in a relatively broader range.

The present invention was made for solving the above-mentioned problems, and an object of the present invention is to provide an optical image measuring device that is capable of measuring, with high accuracy, the physical quantity of a measured object based on a plurality of OCT images in which different sites of the measured object are depicted.

Means for Solving the Problem

In order to achieve the aforementioned objects, a first aspect of the present invention is an optical image measuring device, comprising: an optical system configured to split a low-coherence light into a signal light and a reference light, split an optical path of the reference light into a plurality of optical paths having different optical path lengths to split the reference light into a plurality of reference lights, make the plurality of reference lights propagated through the plurality of optical paths, respectively, interfere with the signal light propagated through a measured object, and generate an interference light that reflects a morphology in each of a plurality of depth positions of the measured object; a detector configured to detect the generated interference light to generate a detection signal; an image forming part configured to form a plurality of tomographic images each representing the morphology of the measured object in each of the plurality of depth positions based on the generated detection signal; and an analyzer configured to analyze the plurality of tomographic images to obtain a predetermined physical quantity of the measured object.

Further, a second aspect of the present invention is the optical image measuring device according to the first aspect, in which: the optical system includes a beam splitter configured to split the reference light having been split from the low-coherence light into the plurality of reference lights, and reference mirrors placed on the respective optical paths of the plurality of reference lights; the beam splitter is configured to compose the plurality of reference lights respectively reflected by the reference mirrors; and the optical system is configured to make the plurality of reference lights having been composed interfere with the signal light to generate the interference light.

Further, a third aspect of the present invention is the optical image measuring device according to the first aspect, in which the optical system includes an optical member configured to extend an optical path length of part of the reference light having been split from the low-coherence light, and a reference mirror configured to reflect the part of the reference light with the optical path extended by the optical member and other part of the reference light, the optical system being configured to make the reference light reflected by the reference mirror interfere with the signal light to generate the interference light.

Further, a fourth aspect of the present invention is the optical image measuring device according to the first aspect, in which the analyzer is configured to obtain, as the predetermined physical quantity, a distance between a position in one tomographic image of the plurality of tomographic images and a position in other tomographic image.

Further, a fifth aspect of the present invention is the optical image measuring device according to the fourth aspect, in which: the measured object is a living eye; the plurality of reference lights include a first reference light propagating on a first optical path having an optical path length corresponding to a retina of the living eye, and a second reference light propagating on a second optical path having an optical path length corresponding to a cornea of the living eye; the image forming part is configured to extract a first signal component corresponding to an interference component of the first reference light and the signal light reflected by the retina from the detection signal to form a first tomographic image showing a morphology of the retina as the one tomographic image, and extract a second signal component corresponding to an interference component of the second reference light and the signal light reflected by the cornea from the detection signal to form a second tomographic image showing a morphology of the cornea as the other tomographic image; and the analyzer is configured to analyze the first and second tomographic images to obtain a corneo-retinal distance of the living eye.

Further, a sixth aspect of the present invention is the optical image measuring device according to the fifth aspect, in which: the first optical path and the second optical path have an optical path length difference substantially equal to a standard value of the corneo-retinal distance; and the analyzer is configured to divide the standard value by a value of a refractive index of an ocular optical system included in ocular optical information stored in advance, and obtain the corneo-retinal distance based on the value of a quotient and the first and second tomographic images.

Further, a seventh aspect of the present invention is the optical image measuring device according to the fifth aspect, in which the analyzer includes a magnification calculator configured to obtain, as the predetermined physical quantity, a magnification of an ocular optical system of the living eye based on the obtained corneo-retinal distance.

Further, an eighth aspect of the present invention is the optical image measuring device according to the seventh aspect, in which: the magnification calculator is configured to obtain the magnification based on optical information of the ocular optical system included in ocular optical information stored in advance and the obtained corneo-retinal distance.

Further, a ninth aspect of the present invention is the optical image measuring device according to the eighth aspect, in which: the ocular optical information includes a value of a radius of curvature of each of a back face and front face of the cornea, a value of a thickness of the cornea, a value of a refractive index of the cornea, a value of a radius of curvature of each of a back face and front face of a crystalline lens, a value of a thickness of the crystalline lens, a value of a refractive index of the crystalline lens, a value of a refractive index of a vitreous body, and a value of an anterior segment distance representing a distance between the front face of the cornea and the back face of the crystalline lens; and the magnification calculator is configured to subtract the value of the anterior segment distance from the corneo-retinal distance to calculate a posterior segment distance representing a distance between the back face of the crystalline lens and the surface of the retina, form an eye model based on the ocular optical information and the posterior segment distance, and obtain the magnification based on the eye model.

Further, a tenth aspect of the present invention is the optical image measuring device according to the ninth aspect, further comprising an alignment part configured to execute position matching of the optical system with respect to the living eye. In the optical image measuring device: the analyzer includes a radius-of-corneal-curvature calculator configured to specify a position within a frame of the second tomographic image based on the interference light generated by the optical system after the position matching, and obtain a radius of corneal curvature of the living eye based on the specified position; and the magnification calculator is configured to form the eye model based on the obtained radius of corneal curvature, instead of the value of the radius of corneal curvature included in the ocular optical system.

Further, an eleventh aspect of the present invention is the optical image measuring device according to the ninth aspect, further comprising an alignment part configured to execute position matching of the optical system with respect to the living eye. In the optical image measuring device: the analyzer includes a radius-of-corneal-curvature calculator configured to obtain a radius of corneal curvature of the living eye based on the optical path length of the second optical path when the interference light is generated by the optical system after the position matching; and the magnification calculator is configured to form the eye model based on the obtained radius of corneal curvature, instead of the value of the radius of corneal curvature included in the ocular optical system.

Further, a twelfth aspect of the present invention is the optical image measuring device according to the ninth aspect, in which: the optical system includes a scanner configured to scan a target position of the signal light on the living eye; the analyzer includes a specifying part configured to, based on the eye model and the obtained magnification, specify a scan aspect of the signal light by the scanner to radiate the signal light to a predetermined position of the retina; the optical system is configured to split a new low-coherence light into a signal light and a reference light and, while causing the scanner to scan with the new signal light based on the specified scan aspect, make the new reference light propagated on the first optical path interfere with the new signal light propagated through the retina to generate a new interference light; the detector is configured to detect the new interference light to generate a new detection signal; and the image forming part is configured to form a new tomographic image of the retina, based on the new detection signal.

Further, a thirteenth aspect of the present invention is the optical image measuring device according to the twelfth aspect, in which the specifying part is configured to, by executing a ray tracing calculation based on the eye model and the obtained magnification, specify the scan aspect to radiate the signal light to the predetermined position of the retina of the eye model.

Further, a fourteenth aspect of the present invention is the optical image measuring device according to the twelfth aspect, in which the specifying part is configured to specify the scan aspect for scanning the target position of the signal light along a circular trajectory that is centered on an optic papilla center of the retina and that has a predetermined radius.

Further, a fifteenth aspect of the present invention is the optical image measuring device according to the twelfth aspect, in which the analyzer is configured to obtain a retinal thickness of the living eye based on the new tomographic image.

Effect of the Invention

The optical image measuring device according to the present invention splits a low-coherence light into a signal light and a reference light, and further splits the reference light into a plurality of reference lights. Moreover, the optical image measuring device according to the present invention makes the reference lights respectively propagated through a plurality of optical paths interfere with the signal light propagated through a measured object, generates an interference light that reflects the morphology in each of the depth positions of the measured object, and forms a plurality of tomographic images of the measured object based on the result of detection of the interference light. Then, the optical image measuring device according to the present invention analyzes these tomographic images and obtains a predetermined physical quantity of the measured object.

Since the optical image measuring device that acts in the above manner is capable of simultaneously executing measurement of a plurality of sites of a measured object, it is possible to measure, with high accuracy, the physical quantity of the measured object depicted in tomographic images (OCT images) of these sites.

Figure 1:
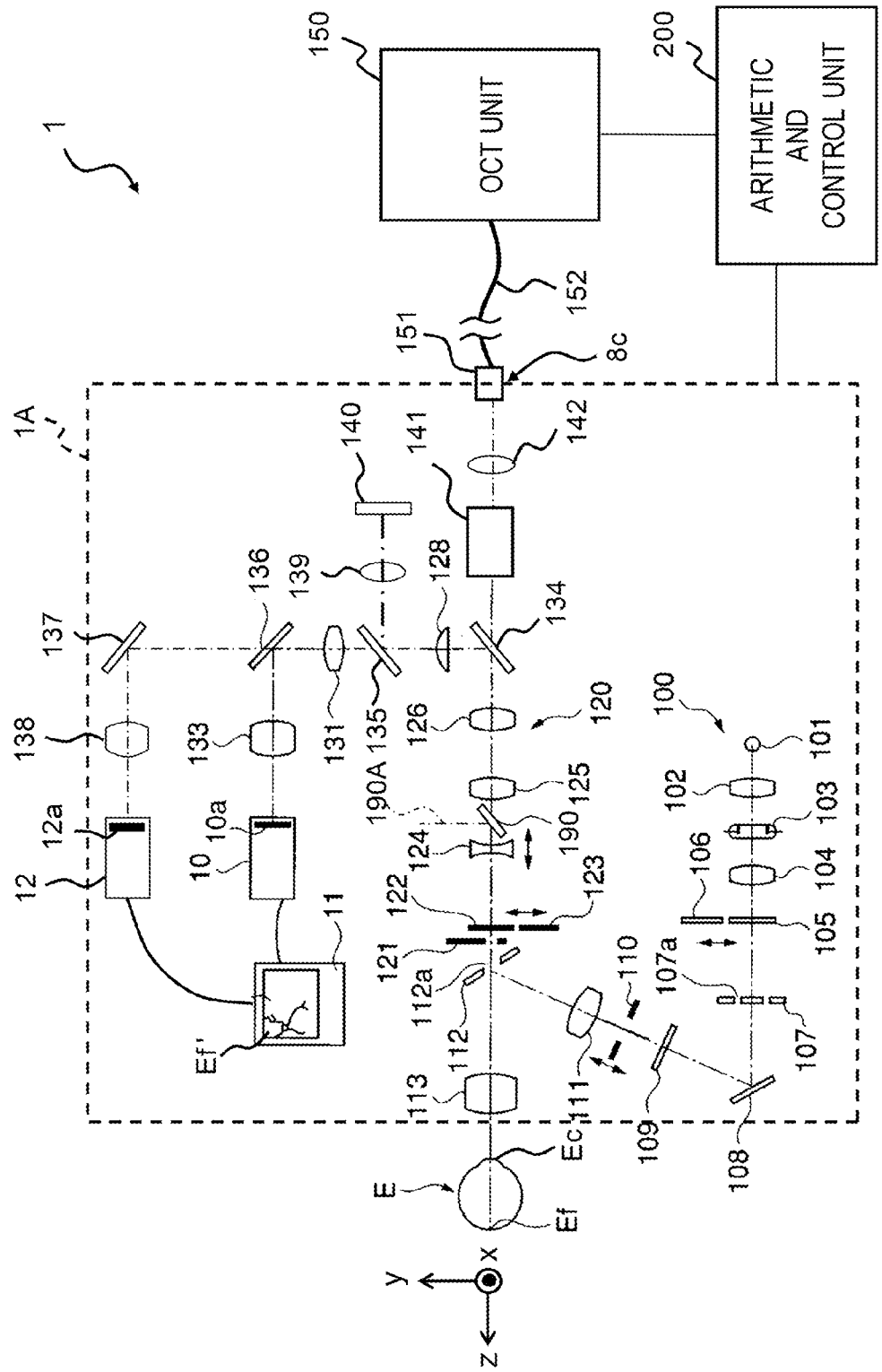
FIG. 1 is a schematic configuration view showing an example of an entire configuration of an embodiment of an optical image measuring device according to the present invention.

DESCRIPTION OF REFERENCE NUMERALS AND SYMBOLS 1 optical image measuring device
1A retinal camera unit
141 scan unit
150 OCT unit
160 low-coherence light source
174a, 174b reference mirror
176a, 176b reference mirror drive mechanism
180 spectrometer
184 CCD
190A alignment optical system
200 arithmetic and control unit
210 controller
211 main controller
212 memory 212a ocular optical information
220 image forming part
221 interference component extracting part
230 image processor
231 analysis processor
232 intraocular distance calculator
233 magnification calculator
234 scan aspect specifying part
235 corneal curvature calculator
240 display part
250 manipulator

BEST MODE FOR CARRYING OUT THE INVENTION

An example of an embodiment of an optical image measuring device according to the present invention will be described in detail with reference to the drawings. In this embodiment, a device that is used in the ophthalmologic field to acquire an OCT image of a living eye will be described. A living eye is moving at all times due to eye movement such as involuntary eye movement, heartbeats, and so on. A like effect can be obtained by a like configuration also at the time of acquisition of an OCT image of a measured object (particularly a measured object involving movement) other than a living eye.

In this embodiment, a configuration to which a Fourier-Domain-type method is applied will be described in detail. To be specific, in this embodiment, an optical image measuring device provided with almost the same configuration as the device disclosed in Patent Document 5 will be picked up. In a case that another configuration is applied, application of a similar configuration to that of this embodiment makes it possible to obtain similar actions and effects. For example, it is possible to apply the configuration according to this embodiment to any type of OCT device that scans with a signal light and executes measurement as in the Swept Source type. Besides, it is also possible to apply the configuration according to this embodiment to an OCT technique, such as the full-field type, in which a scan with a signal light is not executed.

[Configuration]

An optical image measuring device 1, as shown in FIG. 1, includes a retinal camera unit 1A, an OCT unit 150, and an arithmetic and control unit 200. The retinal camera unit 1A has almost the same optical system as a conventional retinal camera. A retinal camera is a device that photographs the fundus oculi and acquires a two-dimensional image. Moreover, a retinal camera is utilized for photographing the morphology of fundus oculi blood vessels. The OCT unit 150 houses an optical system for acquiring an OCT image of an eye. The arithmetic and control unit 200 is provided with a computer that executes various arithmetic processes, control processes, and so on.

To the OCT unit 150, one end of a connection line 152 is attached. To the other end of the connection line 152, a connector part 151 that connects the connection line 152 to the retinal camera unit 1A is attached. An optical fiber 152a runs through inside the connection line 152 (refer to FIG. 4). The OCT unit 150 and the retinal camera unit 1A are optically connected via the connection line 152. The arithmetic and control unit 200 is connected to both the retinal camera unit 1A and the OCT unit 150 via a communication line that transmits electric signals.

[Retinal Camera Unit]

The retinal camera unit 1A has an optical system for forming a two-dimensional image showing the morphology of the fundus oculi surface. A two-dimensional image of the fundus oculi surface includes a color image and a monochrome image obtained by photographing the fundus oculi surface and a fluorescent image (a fluorescein angiography image, an indocyanine green fluorescent image, and so on).

Like a conventional retinal camera, the retinal camera unit 1A is provided with an illumination optical system 100 and an imaging optical system 120. The illumination optical system 100 radiates an illumination light to a fundus oculi Ef. The imaging optical system 120 leads a fundus oculi reflected light of the illumination light to imaging devices 10 and 12. Moreover, the imaging optical system 120 leads a signal light coming from the OCT unit 150 to an eye E, and also leads the signal light propagated through the eye E to the OCT unit 150.

As in a conventional retinal camera, the illumination optical system 100 includes an observation light source 101, a condenser lens 102, an imaging light source 103, a condenser lens 104, exciter filters 105 and 106, a ring transparent plate 107 (a ring slit 107a), a mirror 108, an LCD (Liquid Crystal Display) 109, an illumination diaphragm 110, a relay lens 111, an aperture mirror 112, and an objective lens 113.

The observation light source 101 outputs an illumination light including a wavelength of a visible region in the range from about 400 to 700 nm, for example. The imaging light source 103 outputs an illumination light including a wavelength of a near-infrared region in the range from about 700 to 800 nm, for example. This near-infrared light is set so as to have a shorter wavelength than a light used in the OCT unit 150.

The illumination light outputted from the observation light source 101 reaches the aperture mirror 112 via the condenser lenses 102 and 104, (the exciter filters 105 and 106,) the ring transparent plate 107, the mirror 108, the LCD 109, the illumination diaphragm 110, and the relay lens 111. Besides, this illumination light is reflected by the aperture mirror 112 to enter the eye E via the objective lens 113 and illuminate the fundus oculi Ef. On the other hand, the illumination light outputted from the imaging light source 103 enters the eye E via a path from the condenser lens 104 to the objective lens 113, and illuminates the fundus oculi Ef.

The imaging optical system 120 includes the objective lens 113, (an aperture 112a of) the aperture mirror 112, an imaging diaphragm 121, barrier filters 122 and 123, a magnifying lens 124, a relay lens 125, an imaging lens 126, a dichroic mirror 134, a field lens 128, a half mirror 135, a relay lens 131, a dichroic mirror 136, an imaging lens 133, the imaging device 10, a reflection mirror 137, an imaging lens 138, the imaging device 12, a lens 139, and an LCD 140. The imaging optical system 120 has almost the same configuration as in a conventional retinal camera.

The dichroic mirror 134 reflects the fundus oculi reflected light (having a wavelength included in the range from about 400 to 800 nm) of the illumination light coming from the illumination optical system 100. Moreover, the dichroic mirror 134 transmits a signal light LS (having a wavelength included in the range from about 800 to 900 nm, for example; refer to FIG. 4) coming from the OCT unit 150.

The dichroic mirror 136 transmits the fundus oculi reflected light of the illumination light coming from the observation light source 101. Moreover, the dichroic mirror 136 reflects the fundus oculi reflected light of the illumination light coming from the imaging light source 103.

The LCD 140 displays a fixation target (an internal fixation target) for fixating the eye E. The light from the LCD 140 is focused by the lens 139, reflected by the half mirror 135, propagated through the field lens 128, and reflected by the dichroic mirror 134. Furthermore, this light is propagated through the imaging lens 126, the relay lens 125, the magnifying lens 124, the (aperture 112a of the) aperture mirror 112, the objective lens 113 and so on, and enters the eye E. Consequently, the internal fixation target is projected to the fundus oculi Ef.

By changing a display position of the internal fixation target by the LCD 140, it is possible to change a fixation direction of the eye E.

The fixation direction of the eye E is a fixation direction for acquiring an image centered on the macula of the fundus oculi Ef, a fixation direction for acquiring an image centered on the optic papilla, a fixation direction for acquiring an image centered on the fundus oculi center between the macula and the optic papilla, and so on, as in conventional retinal cameras, for example.

The imaging device 10 includes an image pick-up element 10a.

The imaging device 10 is specifically capable of detecting a light of a wavelength in the near-infrared region. In other words, the imaging device 10 functions as an infrared TV camera that detects a near-infrared light. The imaging device 10 detects a near-infrared light and outputs video signals. The image pick-up element 10a is any kind of image pick-up element (area sensor) such as a CCD (Charge Coupled Device) or a CMOS (Complementary Metal Oxide Semiconductor), for example.

The imaging device 12 includes an image pick-up element 12a.

The imaging device 12 is specifically capable of detecting a light of a wavelength in the visible region. In other words, the imaging device 12 functions as a TV camera that detects a visible light. The imaging device 12 detects a visible light and outputs video signals.

Like the image pick-up element 10a, the image pick-up element 12a is composed of any kind of image pick-up element (area sensor).

A touch panel monitor 11 displays a fundus oculi image Ef' based on the video signals from the respective image pick-up elements 10a and 12a. Moreover, the video signals are transmitted to the arithmetic and control unit 200.

The retinal camera unit 1A is provided with a scan unit 141 and a lens 142. The scan unit 141 scans a target position on the eye E (for example, the fundus oculi Ef) with the signal light LS outputted from the OCT unit 150. The scan unit 141 is an example of a "scanner" of the present invention.

The scan unit 141 scans with the signal light LS on the xy-plane shown in FIG. 1. For this purpose, the scan unit 141 is provided with, for example, a Galvano mirror for scanning in the x-direction and a Galvano mirror for scanning in the y-direction.

On an optical path between the magnifying lens 124 and the relay lens 125, a half mirror 190 is formed at a slant. The half mirror 190 acts to compose an optical path of an alignment optical system 190A shown in FIG. 2A and an optical path of the imaging optical system 120 (an imaging optical path). The alignment optical system 190A is an optical system for projecting, to the eye E, an alignment bright point used for position matching of the optical system with respect to the eye E.

This alignment bright point is used for both an alignment to make an apex position of a cornea Ec of the eye E (a corneal apex) match the optical axes of the optical systems 100 and 120 (an alignment in the xy-direction shown in FIG. 1) and an alignment of a distance between the eye E and the optical systems 100 and 120 (the z-direction in FIG. 1; a working distance; a distance between the cornea Ec (the corneal apex) of the eye E and the objective lens 113) (for example, refer to Japanese Unexamined Patent Application Publication No. 11-4808).

Figure 2A:
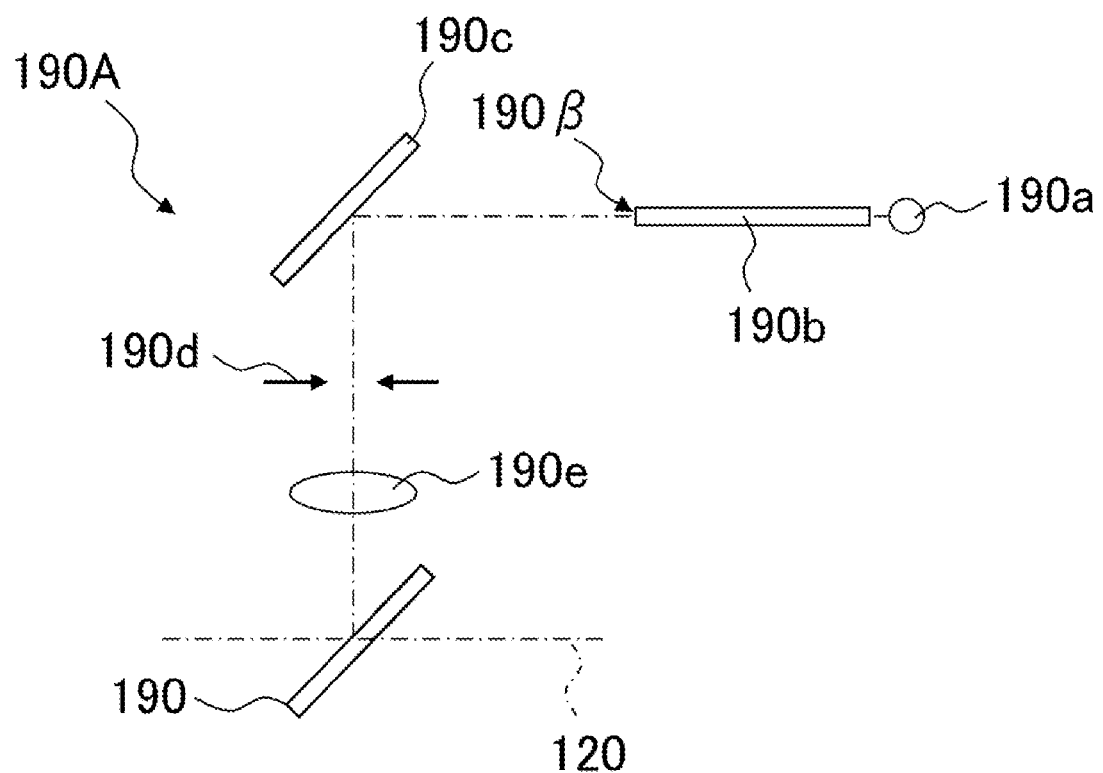
FIG. 2 is a schematic configuration view showing an example of a configuration of an alignment optical system of the embodiment of the optical image measuring device according to the present invention.

The alignment optical system 190A, as shown in FIG. 2A, includes the half mirror 190, an alignment light source 190a, a light guide 190b, a reflection mirror 190c, a two-hole aperture 190d, and a relay lens 190e. The alignment light source 190a, for example, includes a light source such as an LED that outputs a light of near-infrared region (an alignment light).

Figure 2B:
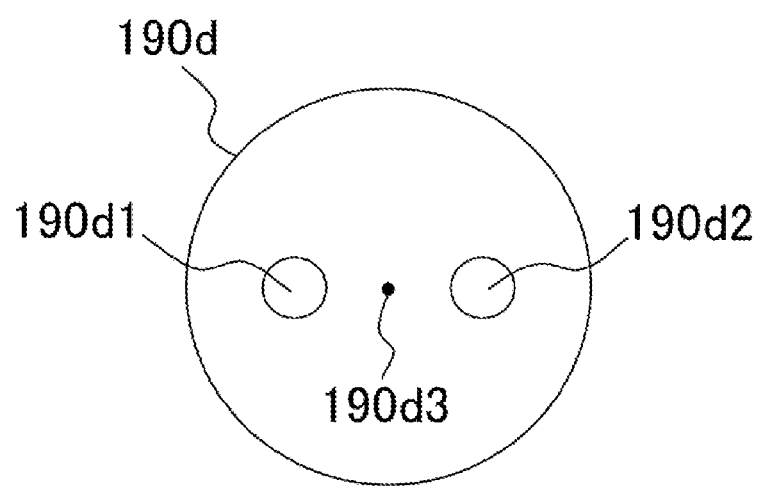

The two-hole aperture 190d has two holes 190d1 and 190d2 as shown in FIG. 2B. The holes 190d1 and 190d2 are formed in symmetrical positions with respect to a center position 190d3 of the disk-like two-hole aperture 190d, for example. The two-hole aperture 190d is mounted so that the center position 190d3 is located on the optical path of the alignment optical system 190A.

The alignment light emitted from an emission end 190β of the light guide 190b is reflected by the reflection mirror 190c and led to the two-hole aperture 190d. The alignment light (or part thereof) having passed through the holes 190d1 and 190d2 of the two-hole aperture 190d is propagated through the relay lens 190e, reflected by the half mirror 190, and led to the aperture mirror 112. At this moment, the relay lens 190e performs intermediate imaging of an image of the emission end 190β of the light guide 190b in the center position of the aperture 112a of the aperture mirror 112 (a position on the optical axis of the imaging optical system 120). The alignment light having passed through the aperture 112a of the aperture mirror 112 is projected to the cornea Ec of the eye E via the objective lens 113.

Here, in a case that a positional relation between the eye E and the retinal camera unit 1A (the objective lens 113) is proper, that is, in a case that a distance between the eye E and the retinal camera unit 1A (a working distance) is proper and the optical axis of the optical system of the retinal camera unit 1A (substantially) matches the axis of the eye E, two light fluxes (alignment light fluxes) formed by the two-hole aperture 190d are projected to the eye E so as to respectively form images at intermediate positions between the corneal apex and the corneal curvature center.

The cornea reflected lights of the two alignment light fluxes (the alignment light) are received by, for example, an image pick-up element 10a via the imaging optical system 120. Images captured by the image pick-up elements 10a are displayed on a display device such as a display (described later) of the touch panel monitor 11 or the arithmetic and control unit 200. A display aspect of the alignment light in this case is shown in FIGS. 3A and 3B.

Figure 3A:
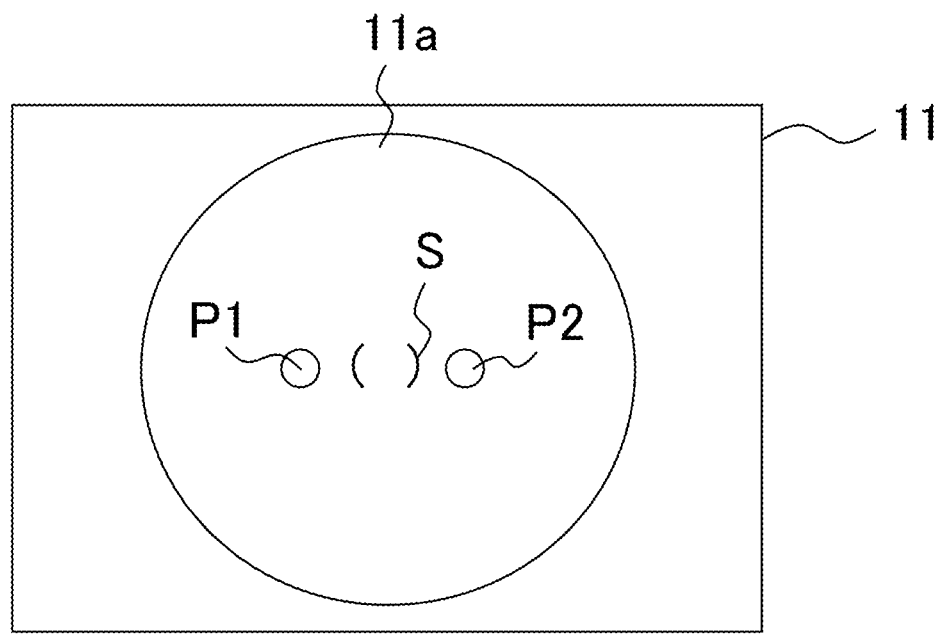
FIG. 3 is a schematic view for describing an example of an alignment operation by the embodiment of the optical image measuring device according to the present invention.
Figure 3B:
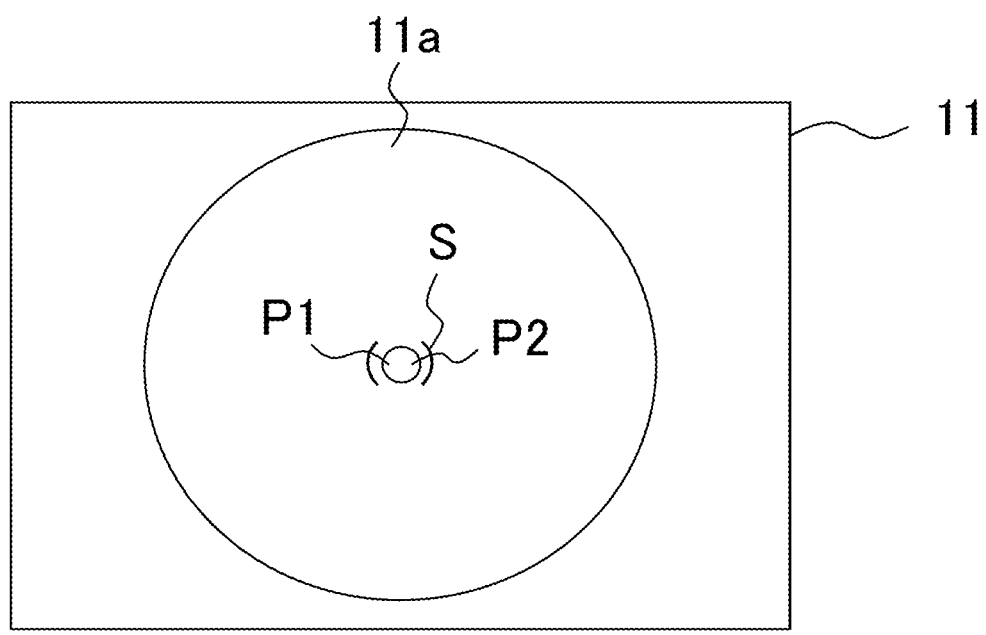

Reference symbol S in FIGS. 3A and 3B denotes a scale having a parenthetical shape, and reference symbols P1 and P2 denote received images of the two alignment light fluxes (alignment bright points). The scale S is displayed on the display or the like so that the center position matches the optical axis of the imaging optical system 120.

In a case that the position of the eye E is off the position of the retinal camera unit 1A in the vertical direction (the y-direction) and the horizontal direction (the x-direction), the alignment bright points P1 and P2 are displayed in positions off the scale S in the vertical direction and the horizontal direction as shown in FIG. 3A. Moreover, in a case that the working distance is not proper, the alignment bright points P1 and P2 are displayed in separate positions.

On the other hand, in a case that the positions in the xy-directions of the eye E and the retinal camera unit 1A coincide and the working distance is proper, the alignment bright points P1 and P2 are displayed within the scale S in the superposed state as shown in FIG. 3B. The examiner executes alignment by adjusting the positional relation between the eye E and the retinal camera unit 1A so that the alignment bright points P1 and P2 are superposed on each other and displayed within the scale S. The adjustment of the positional relation between the eye E and the retinal camera unit 1A is executed by moving the optical system of the retinal camera unit 1A on a movable table as in a conventional retinal camera for example.

The alignment optical system 190A and an optical element of the imaging optical system 120 for leading the alignment light to the eye E compose one example of an "alignment part" of the present invention.

[OCT Unit]

Figure 4:
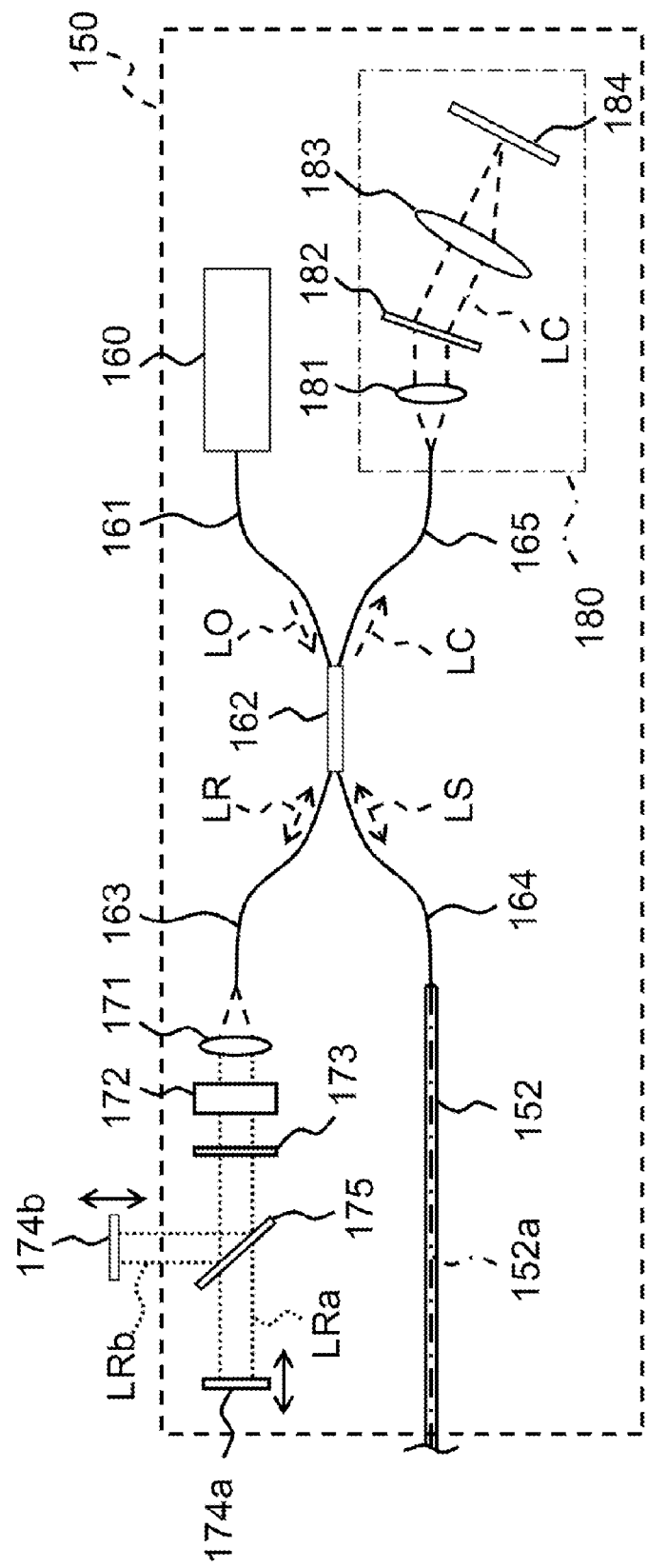
FIG. 4 is a schematic configuration view showing an example of a configuration of an OCT unit in the embodiment of the optical image measuring device according to the present invention.

A configuration of the OCT unit 150 will be described with reference to FIG. 4. The OCT unit 150 has an optical system like that of a conventional Fourier-Domain-type optical image measuring device.

That is to say, the OCT unit 150 has: an optical system that splits a low-coherence light into a reference light and a signal light and makes the signal light propagated through the eye and the reference light propagated through a reference object interfere with each other to generate an interference light; and a detector that detects this interference light. The result of the detection of the interference light (a detection signal) is transmitted to the arithmetic and control unit 200.

A low-coherence light source 160 is a broadband light source that outputs a broadband low-coherence light L0. As this broadband light source, for example, a super luminescent diode (SLD), a light emitting diode (LED) and the like can be used.

For example, the low-coherence light L0 includes a light of a wavelength in the near-infrared region and has a temporal coherence length of about tens of micrometers. The low-coherence light L0 includes a longer wavelength than the illumination light of the retinal camera unit 1A (a wavelength of about 400-800 nm), for example, a wavelength in the range from about 800 to 900 nm.

The low-coherence light L0 outputted from the low-coherence light source 160 is led to an optical coupler 162 through an optical fiber 161. The optical fiber 161 is composed of, for example, a single mode fiber or a PM (polarization maintaining) fiber.

The optical coupler 162 has functions of both a part that splits the low-coherence light L0 into the reference light LR and the signal light LS (a splitter) and a part that superposes lights (a coupler), but will be idiomatically referred to as an "optical coupler" herein.

The reference light LR generated by the optical coupler 162 is led by an optical fiber 163 composed of a single mode fiber or the like, and is emitted from the end face of the fiber. Furthermore, the reference light LR is collimated by a collimator lens 171 and propagated through a glass block 172 and a density filter 173.

Unlike a conventional optical image measuring device having a single reference object (reference mirror), the optical image measuring device 1 according to this embodiment is provided with a plurality of (two) reference mirrors 174a and 174b.

Figure 5:
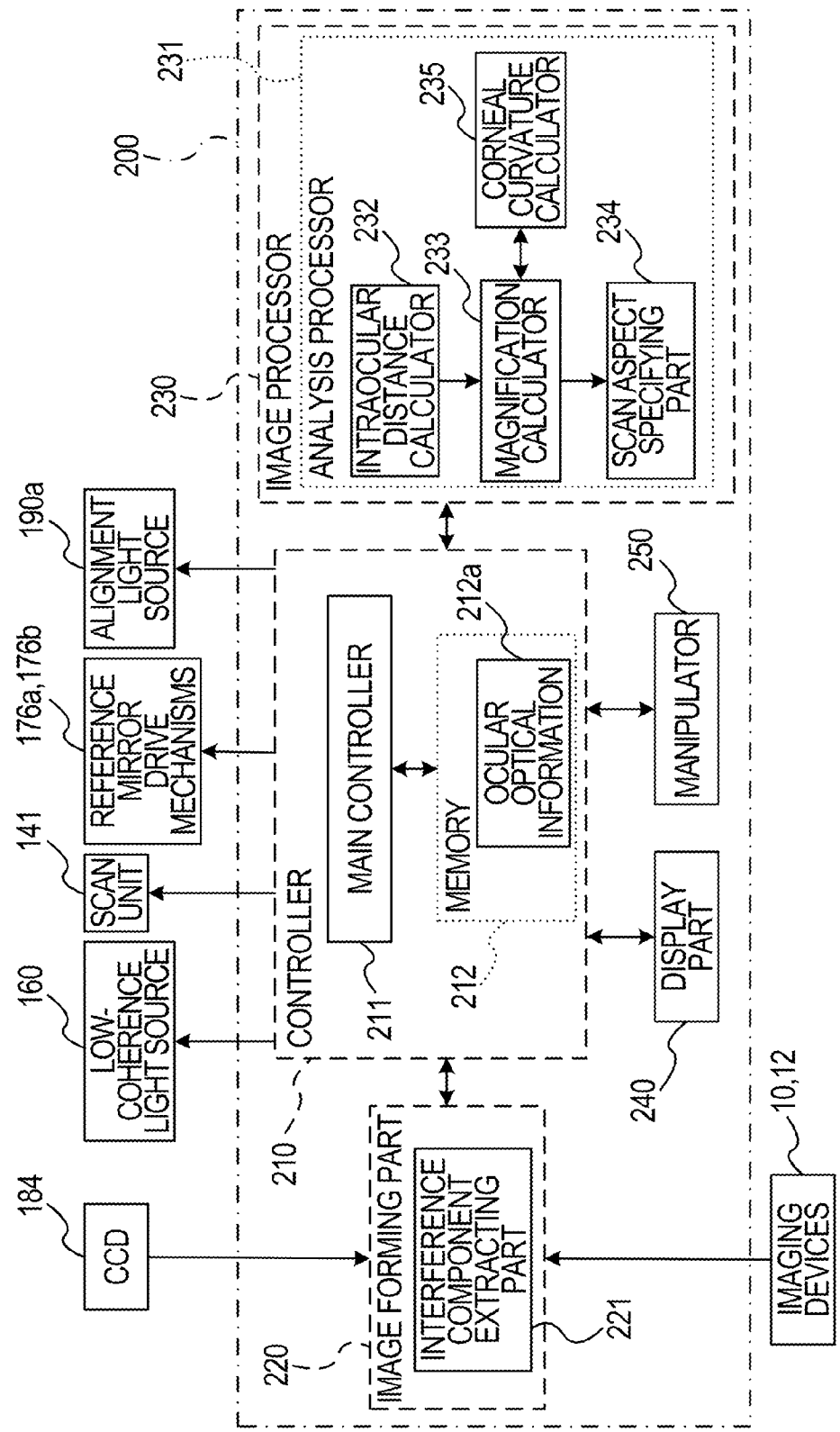
FIG. 5 is a schematic block diagram showing an example of a configuration of a control system of the embodiment of the optical image measuring device according to the present invention.

The respective reference mirrors 174a and 174b are moved in travelling directions (directions of double-sided arrows shown in FIG. 4) of first and second reference lights LRa and LRb by a driving mechanism described later (refer to FIG. 5). Thus, in accordance with the axial length of the eye E, the working distance and so on, it is possible to ensure the optical path lengths of the first and second reference lights LRa and LRb. Moreover, by moving the respective reference mirrors 174a and 174b, it is possible to measure various depth positions of the eye E.

The optical path via the reference mirror 174a is referred to as a first optical path, and the optical path via the reference mirror 174b is referred to as a second optical path. The reference mirrors 174a and 174b are mounted so that the optical path length of the first optical path and the optical path length of the second optical path are different.

That is to say, the reference mirrors 174a and 174b are mounted so that distances to a beam splitter 175 become different from each other. For example, the reference mirrors 174a and 174b are mounted so that an optical path length difference between the first optical path and the second optical path is substantially equal to a distance between the cornea and the retina (a corneo-retinal distance). As this corneo-retinal distance, for example, it is possible to use a standard value of a distance between the cornea and the retina, such as a value of the axial length obtained from a Gullstrand schematic eye and a value obtained by statistically processing the examination results of many eyes (average value and so on). The corneo-retinal distance does not need to be a distance along the depth direction (the z-direction), and may be a distance along a direction diagonal to the depth direction (for example, may be a distance along the travelling direction of the signal light LS).

The reference light LR transmitted through the density filter 173 is split into the first reference light LRa and the second reference light LRb by the beam splitter 175. The beam splitter 175 is composed of a half mirror, for example. The first reference light LRa generated by the beam splitter 175 is reflected by the (first) reference mirror 174a to return to the beam splitter 175. On the other hand, the second reference light LRb generated by the beam splitter 175 is reflected by the (second) reference mirror 174b to return to the beam splitter 175. The beam splitter 175 composes the reference lights LRa and LRb having returned thereto.

The composed light (also referred to as the reference light LR) of the reference lights LRa and LRb generated by the beam splitter 175 is propagated through the density filter 173 and the glass block 172, focused to the fiber end face of the optical fiber 163 by the collimator lens 171, and led to the optical fiber 163 to the optical coupler 162.

The glass block 172 and the density filter 173 act as a delaying part that makes the optical path lengths (the optical distances) of the reference light LR and the signal light LS match each other. Moreover, the glass block 172 and the density filter 173 act as a dispersion compensating part that makes the dispersion properties of the reference light LR and the signal light LS match each other.

Further, the density filter 173 acts as a neutral density filter that reduces the light amount of the reference light LR. The density filter 173 is composed of, for example, a rotary-type ND (Neutral Density) filter. The density filter 173 is driven to rotate by a driving mechanism that is not shown in the drawings, thereby changing the light amount of the reference light LR that contributes to generation of the interference light LD.

On the other hand, the signal light LS generated by the optical coupler 162 is led to the end of the connection line 152 through an optical fiber 164 composed of a single mode fiber or the like. The optical fiber 164 and the optical fiber 152a may be composed of one optical fiber, or may be integrally formed by joining the end faces of the respective fibers.

The signal light LS is led through the optical fiber 152a and guided to the retinal camera unit 1A. Furthermore, the signal light LS is propagated through the lens 142, the scan unit 141, the dichroic mirror 134, the imaging lens 126, the relay lens 125, the half mirror 190, the magnifying lens 124, the imaging diaphragm 121, the aperture 112a of the aperture mirror 112 and the objective lens 113, and radiated to the eye E. When the signal light LS is radiated to the eye E, the barrier filters 122 and 123 are retracted from the optical path in advance. At this moment, the half mirror 190 may also be retracted from the optical path.

The signal light LS having entered the eye E is reflected at various sites of the eye E. For example, the signal light LS is reflected at the cornea Ec, the crystalline lens, the fundus oculi Ef, and so on. At this moment, the signal light LS is not only reflected at the front faces of the cornea Ec and the fundus oculi Ef but also scattered at a refractive index boundary of the deep part. For example, the signal light LS is reflected not only at the front face of the cornea Ec but also at the back face of the cornea Ec and the layer of the cornea cell.

Moreover, the signal light LS is reflected not only at the front face (retinal surface) of the fundus oculi Ef but also the boundary of cell layers composing the retina, the boundary between the retina and the choroidea, and so on. Moreover, the signal light LS is reflected not only at the front face of the crystalline lens but also at the back face thereof. Therefore, the signal light LS propagated through the eye E includes information that reflects the morphology of the front and back faces of various sites of the eye E, and information that reflects a state of back scatter at the refractive index boundary of the deep tissues, and so on.

The signal light LS propagated through the eye E is guided reversely on the same path as the signal light LS travelling to the eye E, and focused to the end face of the optical fiber 152a. Moreover, the signal light LS enters the OCT unit 150 through the optical fiber 152a, and returns to the optical coupler 162 through the optical fiber 164.

The optical coupler 162 makes the signal light LS having returned through the eye E interfere with the reference light LR having returned after reflected by the reference mirrors 174a and 174b to generate the interference light LC. The interference light LC is led to a spectrometer 180 through an optical fiber 165 composed of a single mode fiber or the like.

The spectrometer 180 detects the spectral components of the interference light LC. The spectrometer 180 includes a collimator lens 181, a diffraction grating 182, an imaging lens 183, and a CCD 184.

The diffraction grating 182 may be either a transmission-type or a reflection-type. Moreover, it is also possible to use another photodetecting device (a line sensor or an area sensor) such as a CMOS, instead of the CCD 184.

The interference light LC having entered the spectrometer 180 is collimated by the collimator lens 181, and divided into spectra by the diffraction grating 182 (spectral resolution). The divided interference light LC is formed into an image on the image pick-up face of the CCD 184 by the imaging lens 183. The CCD 184 detects the respective spectral components of the divided interference light LC and converts the components into electric charges. The CCD 184 accumulates these electric charges and generates detection signals. Furthermore, the CCD 184 transmits these detection signals to the arithmetic and control unit 200. The spectrometer 180 (specifically, the CCD 184) is an example of a "detector" of the present invention.

Although a Michelson-type interferometer is employed in this embodiment, it is possible to employ any type of interferometer such as a Mach-Zehnder-type as necessary.

[Arithmetic and Control Unit]

A configuration of the arithmetic and control unit 200 will be described. The arithmetic and control unit 200 analyzes the detection signals inputted from the CCD 184, and forms an OCT image of the eye E. A target site for forming an OCT image is the fundus oculi Ef, the cornea Ec, the crystalline lens, and so on. An arithmetic process for forming an OCT image is like that of a conventional Fourier-Domain-type OCT device.

Further, the arithmetic and control unit 200 controls each part of the retinal camera unit 1A and the OCT unit 150.

As control of the retinal camera unit 1A, the arithmetic and control unit 200 executes: control of output of the illumination lights by the observation light source 101 and the imaging light source 103; control of insertion/retraction of the exciter filters 105, 106 and the barrier filters 122, 123 to/from the optical path; control of the operation of a display device such as the LCD 140; control of turning on/off of the alignment light source 190a; control of movement of the illumination diaphragm 110 (control of the aperture value); control of the aperture value of the imaging diaphragm 121; control of movement of the magnifying lens 124 (control of the magnification); and so on.

Furthermore, the arithmetic and control unit 200 controls the scan unit 141 to scan with the signal light LS.

Further, as control of the OCT unit 150, the arithmetic and control unit 200 executes: control of output of the low-coherence light L0 by the low-coherence light source 160; control of movement of each of the reference mirrors 174a and 174b; control of the rotation operation of the density filter 173 (an operation to change the reduction amount of the light amount of the reference light LR); control of a time for electric charge accumulation, the timing for electric charge accumulation and the timing for signal transmission by the CCD 184; and so on.

The arithmetic and control unit 200 includes a microprocessor, a RAM, a ROM, a hard disk drive, a keyboard, a mouse, a display, a communication interface, and so on, as in conventional computers. The hard disk drive stores a computer program for controlling the optical image measuring device 1. Moreover, the arithmetic and control unit 200 may be provided with a circuit board dedicated for forming OCT images based on detection signals from the CCD 184.

[Control System]

A configuration of a control system of the optical image measuring device 1 will be described with reference to FIG. 5.

The optical image measuring device 1 is provided with reference mirror drive mechanisms 176a and 176b. The reference mirror drive mechanism 176a moves the reference mirror 174a along the travelling direction of the reference light LRa. The reference mirror drive mechanism 176b moves the reference mirror 174b along the travelling direction of the reference light LRb.

The reference mirror drive mechanisms 176a and 176b each include an actuator and a transmission mechanism. The actuator is composed of a pulse motor, for example. Upon reception of pulse signals from the arithmetic and control unit 200 (the main controller 211), the actuator generates a driving force corresponding to the number of pulses. The transmission mechanism includes a gear, for example. The transmission mechanism transmits the driving force generated by the actuator to the reference mirror 174a, 174b. Thus, the respective reference mirrors 174a and 174b operate under control by the arithmetic and control unit 200.

(Controller)

The control system of the fundus oculi observing device 1 has a configuration centered on a controller 210. The controller 210 includes, for example, the aforementioned microprocessor, RAM, ROM, hard disk drive, and communication interface.

The controller 210 is provided with a main controller 211 and a memory 212. The main controller 211 executes the aforementioned various controls. Moreover, the main controller 211 executes a process of writing data into the memory 212, and a process of reading out the data from the memory 212.

Further, the main controller 211 controls the respective reference mirror drive mechanisms 176a and 176b to move the reference mirrors 174a and 174b. The main controller 211 may control the respective reference mirror drive mechanisms 176a and 176b separately, or may control both the reference mirror drive mechanisms in conjunction. This control in conjunction can be employed in a case that, for example, an optical path length difference between the reference lights LRa and LRb is kept constant at all times. In the case of executing only the control in conjunction, it is possible to configure to move both the reference mirrors 174a and 174b by a single reference mirror drive mechanism.

The memory 212 stores various kinds of data. The data stored in the memory 212 is, for example, image data of OCT images, image data of fundus oculi images Ef, and eye information. The eye information includes information on a subject such as a patient ID and a name, information on an eye such as information on identification of left eye or right eye.

In the memory 212, ocular optical information 212a is stored in advance. The ocular optical information 212a includes information on an ocular optical system. For example, the ocular optical information 212a includes optical information of an ocular optical system.

The ocular optical system includes a cornea, a crystalline lens, and a vitreous body. The ocular optical information 212a includes, as information on the cornea, the radius of curvature of each of the front face (the surface) and the back face of the cornea, the thickness of the cornea, and the refractive index of the cornea. Moreover, the ocular optical information 212a includes, as information on the crystalline lens, the radius of curvature of each of the front face and the back face of the crystalline lens, the thickness of the crystalline lens, and the refractive index of the crystalline lens. Moreover, the ocular optical information 212a includes information on the vitreous body such as the refractive index of the vitreous body. Moreover, the ocular optical information 212a includes information on the structure of the ocular optical system. The information on the structure of the ocular optical system is, for example, information on a distance such as an axial length and an anterior segment distance. The anterior segment distance represents a distance between the front face of the cornea and the back face of the crystalline lens. Moreover, the information on the structure of the ocular optical system may include positional information of components of the ocular optical system, positional information of optical characteristic points (a principal point, a focal point, and so on), and refractive power information of the ocular optical system.

Various kinds of values included in the ocular optical information 212a may be standard values, or may be values obtained by actually examining an eye (measured values). As the standard values, for example, it is possible to use values of the Gullstrand schematic eye. It is also possible to use, as the standard values, values statistically calculated based on the results of examinations on a plurality of eyes. On the other hand, as the measured values, it is possible to individually use the results of the examinations on the respective eyes. In this case, the respective examination results are stored and managed in connection with identification information of the eyes (subjects).

(Image Forming Part)

An image forming part 220 receives the video signals from the imaging devices 10 and 12 and forms image data of the fundus oculi image Ef.

Further, the image forming part 220 forms image data of a tomographic image of the fundus oculi Ef based on the detection signals from the CCD 184. Like the conventional Fourier-Domain OCT technique, this process includes processes such as noise elimination (noise reduction), filtering, and FFT (Fast Fourier Transform).

The image forming part 220 includes, for example, the aforementioned microscope, circuit board, and communication interface. In this specification, "image data" may be identified with an "image" presented based on the image data.

(Interference Component Extracting Part)

The image forming part 220 is provided with an interference component extracting part 221. The interference component extracting part 221 operates when a plurality of sites of the eye E at different depth positions (positions in the z-direction) are simultaneously measured.

Simultaneous measurement of a plurality of sites of the eye E will be described. The optical image measuring device 1 is provided with the two reference mirrors 174a and 174b. These reference mirrors 174a and 174b are mounted so as to make a predetermined optical path length difference as described before. Therefore, the interference light LC includes information (an interference component) representing the morphology of each of the two sites of the eye E separated in the depth direction by a distance corresponding to the optical path length difference. Accordingly, the detection signal outputted from the CCD 184 includes a signal component corresponding to each of the two sites.

For example, in a case that the reference mirrors 174a and 174b are placed in positions corresponding to the fundus oculi Ef and the cornea Ec, respectively, namely, in a case that the optical path length difference is substantially equal to a corneo-retinal distance, the detection signal outputted from the CCD 184 includes a signal component corresponding to the fundus oculi Ef (the retina) and a signal component corresponding to the cornea Ec.

Here, "the reference mirror 174a is placed in a position corresponding to the fundus oculi Ef" means that an optical distance from the optical coupler 162 to the reference mirror 174a is (substantially) equal to a distance from the optical coupler 162 to the fundus oculi Ef. The reference mirror 174b and the cornea Ec are also placed in a like manner. The optical image measuring device 1 generates the interference light LC with the low-coherence light L0, and therefore, functions to selectively form images of the sites of the eye E corresponding to the respective reference mirrors 174a and 174b.

The interference component extracting part 221 extracts two signal components from the detection signal outputted from the CCD 184. An example of this process will be described. The detection signal includes a signal component corresponding to the fundus oculi Ef (a fundus oculi component) and a signal component corresponding to the cornea Ec (a cornea component). The fundus oculi component and the cornea component form frequency components (frequency bands) different from each other in the detection signal. That is to say, the detection signal is a signal in which a frequency component forming the fundus oculi component and a frequency component forming the cornea component are superposed (besides, noise is also included).

The interference component extracting part 221 extracts various frequency components included in the detection signal (after eliminating noise as needed). This process is executed by any sort of frequency resolving process, for example. Furthermore, the interference component extracting part 221 selects the fundus oculi component and the cornea component from among the extracted frequency components. This process can be executed by selecting frequency components determined by measurement in advance, for example. Alternatively, in consideration of a fact that a frequency component other than the fundus oculi component and the cornea component is that resulting from noise, frequency components with high signal intensity may be selected from among the extracted frequency components.

When the fundus oculi component and the cornea component are extracted, the image forming part 220 forms a tomographic image of the fundus oculi Ef based on the fundus oculi component, and also forms a tomographic image of the cornea Ec based on the cornea component.

(Image Processor)

An image processor 230 executes various image processing and analysis processes on the images formed by the image forming part 220.

For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus oculi Ef.

Image data of a three-dimensional image refers to image data that the positions of pixels are defined by the three-dimensional coordinates. The image data of a three-dimensional image is, for example, image data composed of three-dimensionally arranged voxels.

This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display part 240, this pseudo three-dimensional image is displayed.

Further, it is also possible to form stack data of a plurality of tomographic images as the image data of a three-dimensional image.

Stack data is image data obtained by three-dimensionally arranging a plurality of tomographic images obtained along a plurality of scanning lines, based on the positional relation of the scanning lines.

That is to say, stack data is image data obtained by expressing a plurality of tomographic images defined by originally individual two-dimensional coordinate systems by a three-dimensional coordinate system (namely, embedding into a three-dimensional space).

The image processor 230 includes, for example, the aforementioned microprocessor, RAM, ROM, hard disk drive, and circuit board.

(Analysis Processor)

The image processor 230 is provided with an analysis processor 231. The analysis processor 231 analyzes a plurality of tomographic images acquired by simultaneous measurement of a plurality of sites of the eye E, thereby obtaining a predetermined physical quantity of the eye E. Moreover, the analysis processor 231 specifies a scan aspect of the signal light LS based on the obtained physical quantity of the eye E.

The physical quantity generally expresses a physical property, and means a quantity for which a measurement method and a dimension unit are defined. Examples of physical quantity include mass, length, volume, pressure, time, energy, and so on. To be specific, the physical quantity in this embodiment means a quantity that is inherent in an object (the eye E) and objectively measurable, and also a quantity that can be calculated by using the above quantity. In this embodiment, a case of dealing with the intraocular distance, magnification, radius of corneal curvature (corneal curvature), retinal thickness and so on of the eye E as the predetermined physical quantity will be described particularly in detail.

The analysis processor 231 is provided with an intraocular distance calculator 232, a magnification calculator 233, a scan aspect specifying part 234, and a corneal curvature calculator 235. In the case of, for example, using the value of the radius of corneal curvature included in the ocular optical information 212a, and in the case of using an actual measurement value of the radius of corneal curvature of the eye E, it is unnecessary to dispose the corneal curvature calculator 235.

(Intraocular Distance Calculator)

The intraocular distance calculator 232 obtains a distance between a position in one tomographic image of a plurality of tomographic images of the eye E and a position in other tomographic image. To be specific, in this embodiment, the intraocular distance calculator 232 analyzes a tomographic image of the fundus oculi Ef (a fundus oculi tomographic image) and a tomographic image of the cornea Ec (a cornea tomographic image), and obtains a corneo-retinal distance of the eye E. Below, an example of a process executed by the intraocular distance calculator 232 will be described.

The intraocular distance calculator 232 is capable of obtaining any sort of intraocular distance of the eye E other than the corneo-retinal distance. The intraocular distance includes a distance between two points inside the eye E, a distance between one point on the surface and one point inside the eye E, and a distance between two points on the surface of the eye E.

The intraocular distance calculator 232 firstly acquires an optical path length difference between the reference lights LRa and LRb at the time of execution of simultaneous measurement for acquiring a fundus oculi tomographic image and a cornea tomographic image. This optical path length difference can be acquired from the positions of the two reference mirrors 174a and 174b, for example.

As mentioned before, at the time of the simultaneous measurement, it is possible to set an optical path length difference between the reference mirrors 174a and 174b so as to be substantially equal to a standard value of the corneo-retinal distance (an axial length or the like). In this case, the optical path length difference acquired by the intraocular distance calculator 232 is the standard value of the corneo-retinal distance.

As another method for acquiring the optical path length difference, it is possible to obtain the optical path length difference based on the positions of the respective reference mirrors 174a and 174b in the simultaneous measurement. For example, the positions of the respective reference mirrors 174a and 174b can be acquired based on the number of pulses of pulse signals sent from the main controller 211 to the respective reference mirror drive mechanisms 176a and 176b.

Moreover, the positions of the respective reference mirrors 174a and 174b may be detected by a position sensor.

The intraocular distance calculator 232 having acquired the optical path length difference between the reference lights LRa and LRb divides the value of this optical path length difference by the refractive index of the ocular optical system. As this refractive index, it is possible to use a value (a standard value, a measured value) recorded in the ocular optical information 212a, for example. By this calculation, an optical distance expressed by the optical path length difference is converted into a spatial distance.

Subsequently, the intraocular distance calculator 232 obtains the corneo-retinal distance of the eye E based on the obtained spatial distance, the fundus oculi tomographic image and the cornea tomographic image. This calculation process will be described below.

The abovementioned spatial distance is substantially equal to a distance between the fundus oculi tomographic image and the cornea tomographic image. That is to say, the aforementioned spatial distance is substantially equal to an interval in the depth direction between a predetermined position in a frame in which the fundus oculi tomographic image is depicted (for example, the upper end of the frame) and a predetermined position in a frame in which the cornea tomographic image is depicted (the same position as mentioned above).

Consideration of this relation makes it possible to express both the tomographic images in the same coordinate system (particularly the z-coordinate).

The intraocular distance calculator 232 analyzes the fundus oculi tomographic image to specify an image region (an internal limiting membrane region) corresponding to the internal limiting membrane (the retinal surface), and also analyzes the cornea tomographic image to specify an image region (a corneal surface region) corresponding to the corneal surface. This process can be executed by a threshold process based on the pixel value (the brightness value) of pixels composing the tomographic image and a filtering process as conventional. It is also possible to configure to display the fundus oculi tomographic image and the cornea tomographic image so that the operator manually designates the internal limiting membrane region and the corneal surface region on the displayed images (this is true to the following process).

Next, the intraocular distance calculator 232 specifies one point in the internal limiting membrane region (a characteristic point such as an optic papilla center or a macula center), for example. This process can be executed by analyzing the shape of the internal limiting membrane region and specifying a characteristic point (such as a center position of a dent).

Subsequently, the intraocular distance calculator 232 specifies one point in the corneal surface region having the same X-coordinate value (and/or y-coordinate value) as the abovementioned one point in the internal limiting membrane. In a case that the trajectory of the signal light LS radiated to the abovementioned one point in the internal limiting membrane is inclined with respect to the optical axis of the optical system of the retinal camera unit 1A (there is such a case depending on a scan with the signal light LS), one point in the corneal surface region intersecting with the trajectory may be specified.

Then, the intraocular distance calculator 232 refers to the abovementioned coordinate system expressing both the tomographic images, and calculates a distance between the two points based on the coordinate value of the one point in the internal limiting membrane region and the coordinate value of the one point in the corneal surface region. For example, the intraocular distance calculator 232 obtains the distance between the two points by calculating a difference in z-coordinate value between the two points. In a case that the two points are not located on a line extending in the z-direction, it is possible to calculate the distance between the two points by using a general arithmetic expression (square-root of the sum of squares of difference of the respective coordinate values on the three coordinate axes) for obtaining a distance in the xyz-coordinate system. With the abovementioned process, the corneo-retinal distance is obtained from the two tomographic images of the eye E. The acquired corneo-retinal distance (intraocular distance) is sent to the magnification calculator 233.

In the above process example, one point in the corneal surface region is specified after one point in the internal limiting membrane region is specified, but it is also possible to execute the process reversely. For example, it is possible to configure to firstly specify one point corresponding to the corneal apex in the corneal surface region and then specify one point in the internal limiting membrane region corresponding to the one point.

(Magnification Calculator)

The magnification calculator 233 obtains the magnification of the ocular optical system of the eye E based on the corneo-retinal distance obtained by the intraocular distance calculator 232. The magnification calculator 233 is an example of a "magnification calculator" of the present invention. Below, an example of a process executed by the magnification calculator 233 will be described.

The magnification calculator 233 can obtain the magnification of the ocular optical system of the eye E based on, for example, the optical information of the ocular optical system included in the ocular optical information 212a stored in the memory 212, and the corneo-retinal distance obtained by the intraocular distance calculator 232.

As mentioned before, the ocular optical information 212a includes various kinds of optical information of the ocular optical system, such as the radius of curvature of each of the back and front faces of the cornea, the thickness of the cornea, the refractive index of the cornea, the radius of curvature of each of the back and front faces of the crystalline lens, the thickness of the crystalline lens, the refractive index of the crystalline lens, the refractive index of the vitreous body, and the anterior segment distance (a distance between the front face of the cornea and the back face of the crystalline lens).

The magnification calculator 233 firstly subtracts the value of the anterior segment distance from the corneo-retinal distance obtained by the intraocular distance calculator 232, and calculates a distance between the back face of the crystalline lens and the retinal surface (the posterior segment distance).

Next, the magnification calculator 233 forms an eye model based on the calculated posterior segment distance and the ocular optical information 212a. Even if the ocular optical information 212a includes a standard value (a value of the Gullstrand schematic eye or the like), at least the posterior segment distance is a value that reflects the eye E. Therefore, the eye model to be formed reflects the eye E. It is needless to say that the degree of reflection of the eye E is higher as the ocular optical information 212a includes more measured values.

An eye model is a set of a series of physical quantities representing the morphology and property of the eyeball and composition sites thereof, for example, like a schematic eye. The ocular model may be a simple set (a list or the like) of such physical quantities, or may be an image of the eyeball formed based on the physical quantities.

The magnification calculator 233 obtains the magnification of the ocular optical system based on the formed eye model. The value of the obtained magnification is used as the magnification of the ocular optical system of the eye E. A process of obtaining the magnification is executed by, for example, obtaining a projection image obtained by projecting an image of unit length entering the eye E to the fundus oculi Ef (the retinal surface), and calculating the ratio of the length of this projection image to the unit length, by a general ray tracing calculation.

(Scan Aspect Specifying Part)

The scan aspect specifying part 234 specifies a scan aspect of the signal light LS by the scan unit 141 so as to radiate the signal light LS to a predetermined position of the retina of the eye E, based on the obtained magnification and the above eye model. The scan aspect specifying part 234 is an example of a "specifying part" of the present invention.

An example of a process executed by the scan aspect specifying part 234 will be described. In the following process example, a case of scanning a target position of the signal light LS along a circular trajectory that is centered on the optic papilla center and that has a predetermined radius will be described in detail. In this case, it is desirable that the intraocular distance calculator 232 obtains the corneo-retinal distance between one point corresponding to the optic papilla center in the internal limiting membrane region and one point in the cornea tomographic image (described before).

For example, the scan aspect specifying part 234 executes a ray tracing calculation, thereby obtaining an aimed scan aspect of the signal light LS. In this ray tracing calculation, for example, based on the eye model and the magnification, for each position on the abovementioned circular trajectory on the retina of the eye model, an incident trajectory of the signal light LS to the eye model (an incident angle to the eye axis or the optical system axis) such that the signal light LS is radiated to this position is obtained. That is to say, this ray tracing calculation is reverse calculation of such an incident trajectory of the signal light LS that a predetermined position of the retina of the eye model is targeted and the signal light LS is radiated to the target position.

Furthermore, the scan aspect specifying part 234 obtains an operation aspect of the scan unit 141 in which a specified scan aspect is realized. In this process, for example, such a direction of the Galvano mirror within the scan unit 141 that the signal light LS is propagated along the specified incident trajectory is obtained. As the relation between the direction of the Galvano mirror and the propagation trajectory of the signal light LS, a relation obtained in advance may be stored. Moreover, it is possible to configure to calculate backwards such a direction of the Galvano mirror that the signal light LS propagates along a target trajectory, by the ray tracing calculation as described above (the optical system of the retinal camera unit 1A is taken into account).

(Corneal Curvature Calculator)

The corneal curvature calculator 235 obtains the radius of corneal curvature (or the corneal curvature) of the eye E. Since the radius of corneal curvature and the corneal curvature are the reciprocals mutually, one is obtained when the other is obtained. The corneal curvature calculator 235 is one example of a "radius-of-corneal-curvature calculator" of the present invention.

Below, an example of a process executed by the corneal curvature calculator 235 will be described.

As described before, the optical image measuring device 1 is capable of executing position matching of the optical system with respect to the eye E by using the alignment bright points P1 and P2 (refer to FIGS. 2 and 3). In a state that the working distance is proper and the optical axis of the optical system and the axis of the eye E coincide with each other, two alignment light fluxes forming the alignment bright points P1 and P2 form images, respectively, in the intermediate positions between the corneal apex and the corneal curvature center. The working distance is a distance between the corneal apex and the optical system.

The corneal curvature calculator 235 obtains the radius of corneal curvature by utilizing such characteristics of alignment. For this, a fundus oculi tomographic image and a cornea tomographic image are formed by executing simultaneous measurement in a state that the alignment is proper, namely, the two alignment bright points P1 and P2 are superposed.

The corneal curvature calculator 235 obtains, for example, the position of an image corresponding to the corneal surface (the position corresponding to the corneal apex, specifically) within the frame of a cornea tomographic image. In a case that a corneal surface region (the position corresponding to the corneal apex) has been specified by the intraocular distance calculator 232, it is possible to utilize the result of this specification. Then, the corneal curvature calculator 235 calculates the radius of corneal curvature of the eye E based on a displacement of the obtained image position of the corneal surface from a predetermined position (described later).

Another operation example of the corneal curvature calculator 235 will be described. The position of the reference mirror 174b (for the cornea) in simultaneous measurement executed in the proper alignment state as in the above is obtained. In a case that the position of the reference mirror 174b has already been acquired in the process executed by the intraocular distance calculator 232, it is possible to utilize this result. Then, the corneal curvature calculator 235 calculates the radius of corneal curvature of the eye E based on a displacement of the obtained position of the reference mirror 174b from a predetermined position (described later).

A specific example of the process executed by the corneal curvature calculator 235 will be described. In this process example, the radius of corneal curvature is obtained by executing preliminary measurement of a schematic eye and utilizing the result. The radius of corneal curvature of the schematic eye (the radius of curvature of the corneal front face) is set to 8 mm.

In the preliminary measurement, firstly, alignment of the optical system of the retinal camera unit 1A with respect to this schematic eye is executed. Next, the reference mirror 174b is placed in a position for measuring the cornea of the schematic eye, and measurement of the cornea of the schematic eye is executed by operating the OCT unit 150.

Furthermore, based on the result of this measurement, a tomographic image of the cornea of the schematic eye is formed. Then, a position of an image corresponding to the corneal surface within the frame of this tomographic image is obtained (referred to as a reference position). Together with the value of the radius of corneal curvature of the schematic eye, this reference position is stored into, for example, the memory 212. This is the end of the preliminary measurement.

In real measurement (simultaneous measurement of the fundus oculi Ef and the cornea Ec), as mentioned before, the alignment of the optical system with respect to the eye E is executed, the reference mirror 174a is placed in a position for measurement of the fundus oculi Ef, and the reference mirror 174b is placed in a position for measurement of the cornea Ec. Then, the OCT unit 150 is operated so that the simultaneous measurement of the fundus oculi Ef and the cornea Ec is executed. Furthermore, based on the result of this measurement, a fundus oculi tomographic image and a cornea tomographic image are formed.

The corneal curvature calculator 235 obtains the position of an image corresponding to the corneal surface within the frame of this cornea tomographic image. Furthermore, the corneal curvature calculator 235 obtains a displacement of the obtained position of the image of the corneal surface from the reference position obtained in the preliminary measurement. Then, the corneal curvature calculator 235 doubles the value of this displacement and adds 8 mm (the radius of corneal curvature of the schematic eye) to the product, thereby obtaining the radius of corneal curvature of the eye E. In a case that the refractive power of the eye E is taken into consideration, the radius of corneal curvature of the eye E may be obtained by utilizing a measured value, or may be obtained based on the lens position (the position of the magnifying lens 124 or the like) of the optical system.

The process of obtaining the radius of corneal curvature based on the position of the reference mirror 174b can also be executed in a like manner.

(Display Part and Manipulator)

The display part 240 includes a display. The manipulator 250 includes an input device and manipulation device such as a keyboard and a mouse. The manipulator 250 may include various buttons and keys formed on the housing of the fundus oculi observing device 1 or outside thereof.

The display part 240 and the manipulator 250 do not need to be composed as separate devices. For example, like a touch panel LCD, a device in which the display part 240 and the manipulator 250 are formed in one body can be used.

[Scan with Signal Light and Image Processing]

A scan with the signal light LS and an OCT image will be described.

The scan aspect of the signal light LS by the optical image measuring device 1 is, for example, a horizontal scan, vertical scan, cruciform scan, radial scan, circular scan, concentric scan, and helical scan. These scan aspects are selectively used as necessary in consideration of an observation site of the fundus oculi, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory.

With the configuration as described before, the scan unit 141 is capable of scanning with the signal light LS in the x-direction and the y-direction, respectively, and is therefore capable of scanning with the signal light LS along any sort of trajectory on the xy-plane. Thus, it is possible to realize various types of scan aspects as described above.

By scanning with the signal light LS in the aspects as described above, it is possible to form a tomographic image in the depth direction along a scanning line (a scanning trajectory). Moreover, in a case that the interval between scanning lines is narrow, it is possible to form the aforementioned three-dimensional image.

[Operation]

Figure 6:
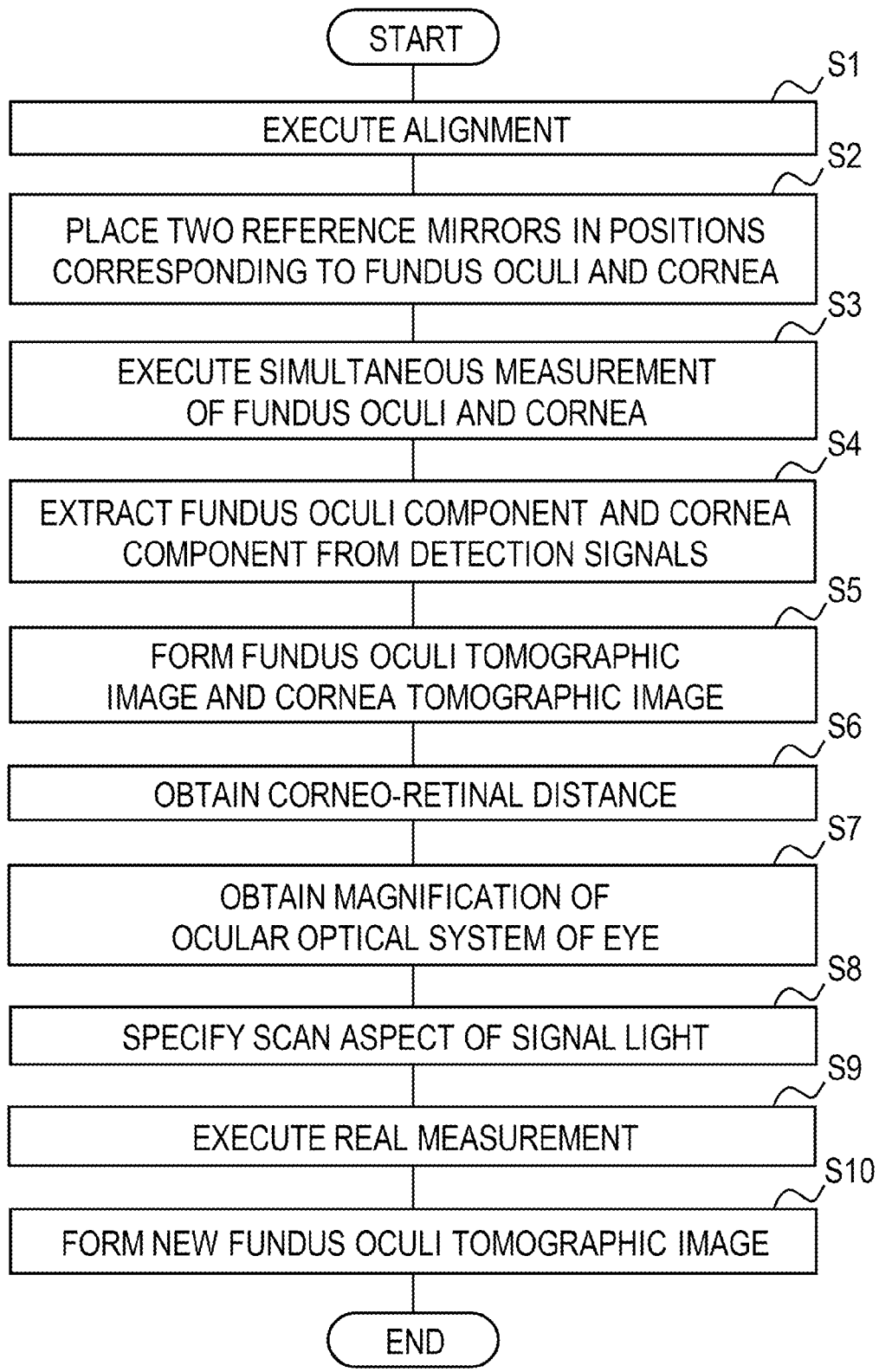
FIG. 6 is a flow chart showing an example of an operation of the embodiment of the optical image measuring device according to the present invention.

An operation of the optical image measuring device 1 will be described. A flow chart shown in FIG. 6 represents an example of the operation of the optical image measuring device 1. The ocular optical information 212a is already stored in the memory 212. Moreover, the value of the radius of corneal curvature of the schematic eye and the reference position of the image of the corneal surface in the preliminary measurement described before are already stored in the memory 212.

Firstly, alignment of the optical system with respect to the eye E is executed (S1). The alignment is executed by adjusting the position of the retinal camera unit 1A while projecting the alignment bright points P1 and P2 to the eye E and observing the condition, as shown in FIG. 3.

Next, the reference mirror 174a is placed in a position corresponding to the fundus oculi Ef, and the reference mirror 174b is placed in a position corresponding to the cornea Ec (S2). As mentioned before, the reference mirrors 174a and 174b are placed in such positions that make an optical path length difference equal to the standard value of the corneo-retinal distance between the reference lights LRa and LRb. To be specific, the reference mirror 174a is placed in a position in which an image of a predetermined site (for example, the retinal surface) of the fundus oculi is clear, and the reference mirror 174b is placed in a position in which an image of a predetermined site (for example, the corneal surface) of the cornea Ec is clear. An operation of moving the reference mirrors 174a and 174b may be manually executed by using the manipulator 250, or may be controlled by the main controller 211 based on the detection signals or signals obtained by processing the detection signals.

When the reference mirrors 174a and 174b are placed in the target positions, the main controller 211 controls the low-coherence light source 160, the scan unit 141, the CCD 184 and so on to execute the simultaneous measurement of the fundus oculi Ef and the cornea Ec (S3). This simultaneous measurement is started in response to a start request with the manipulator 250, for example. Alternatively, the simultaneous measurement may be started automatically in response to completion of the operation of moving the reference mirrors 174a and 174b. At the time of the simultaneous measurement, the eye E is fixated by an internal fixation target as necessary.

The interference component extracting part 221 extracts a fundus oculi component and a cornea component from the detection signals (S4). The image forming part 220 forms a tomographic image of the fundus oculi Ef based on this fundus oculi component, and forms a tomographic image of the cornea Ec based on this cornea component (S5). These tomographic images may be formed in any order.

Alternatively, the processes for forming these images may be in parallel.

The image forming part 220 sends the fundus oculi tomographic image and the cornea tomographic image to the controller 210. The main controller 211 sends the fundus oculi tomographic image and the cornea tomographic image to the image processor 230. Moreover, the main controller 211 reads out the ocular optical information 212a from the memory 212 to send to the image processor 230. Moreover, the main controller 211 reads out various kinds of information (mentioned before) to be referred to by the image processor 230 from the memory 212 to send to the image processor 230.

Figure 7:
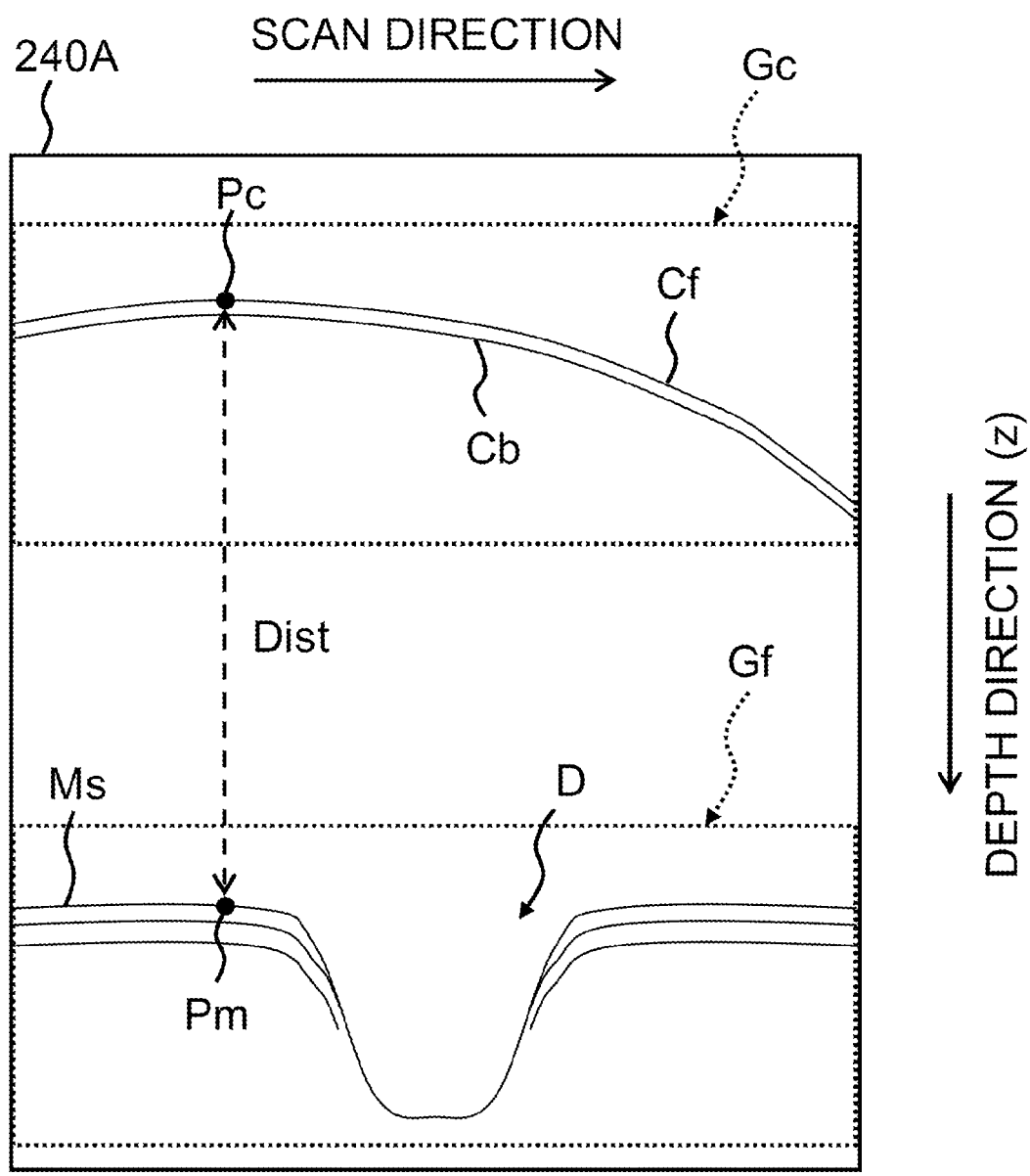
FIG. 7 is a schematic view showing an example of a display aspect of a fundus oculi tomographic image and a cornea tomographic image by the embodiment of the optical image measuring device according to the present invention.

Further, the main controller 211 may cause the display part 240 to display the fundus oculi tomographic image and the cornea tomographic image. An example of a display aspect in this case is shown in FIG. 7. The main controller 211 causes the display part 240 to display a fundus oculi tomographic image Gf and a cornea tomographic image Gc on a (partial region of a) display screen 240A.

In this display aspect, the fundus oculi tomographic image Gf and the cornea tomographic image Gc are placed side by side in the depth direction. At this moment, the tomographic images Gf and Gc may be displayed by the same magnification, or may be displayed by different magnifications. Moreover, a display interval between the tomographic images Gf and Gc may match an actual interval (for example, the standard value of the corneo-retinal distance), or may not match.

The simultaneous measurement for acquiring the tomographic images Gf and Gc is executed with the eye E fixated in a fixation direction for acquiring an image of the optic papilla. The fundus oculi tomographic image Gf depicts the vicinity of an optic papilla D.

Reference symbol Ms denotes an image region (an internal limiting membrane region) corresponding to the retinal surface (the internal limiting membrane). Reference symbol Cf denotes an image region (a corneal surface region) corresponding to the corneal surface (the corneal front face). Reference symbol Cb denotes an image region corresponding to the corneal back face.

The intraocular distance calculator 232 analyzes the fundus oculi tomographic image and the cornea tomographic image, and obtains the corneo-retinal distance of the eye E (S6). On the tomographic images Gf and Gc shown in FIG. 7, the intraocular distance calculator 232 calculates a distance Dist between a point Pc on the corneal surface region Cf (the position of the corneal apex or the like) and a point Pm on the internal limiting membrane region Ms.

Next, the magnification calculator 233 obtains the magnification of the ocular optical system of the eye E based on the corneo-retinal distance obtained in step S6 and the ocular optical information 212a (S7). This process is executed by using an eye model as mentioned before.

Subsequently, the scan aspect specifying part 234 specifies a scan aspect of the signal light LS to radiate the signal light LS to a predetermined position of the retina of the eye E, based on the magnification obtained in step S7 and the above-mentioned eye model (S8). This process is executed by using a ray tracing calculation as mentioned before. Moreover, in a case that the tomographic images Gf and Gc shown in FIG. 7 are acquired, the scan aspect specifying part 234 specifies a scan aspect for scanning a target position of the signal light LS along a circular trajectory that is centered on the center position of the optic papilla D and having a predetermined radius. The specified scan aspect is sent to the controller 210.

The main controller 211 controls the low-coherence light source 160, the scan unit 141, the CCD 184 and so on to execute the following real measurement (S9). That is to say, the main controller 211 controls to output a new low-coherence light, scan with a new signal light based on the new low-coherence light based on the scan aspect specified in step S8, and make a new reference light propagated thorough the first optical path interfere with a new signal light propagated though the retina to generate a new interference light.

The CCD 184 detects this new interference light and outputs new detection signals. Furthermore, the image forming part 220 forms a new tomographic image of the retina (the fundus oculi Ef) based on the new detection signals (S10). This new tomographic image is, for example, a tomographic image along a circular trajectory that is centered on the optical papilla center of the fundus oculi Ef and that has a predetermined radius. The tomographic image of the fundus oculi Ef formed in step S10 is stored into the memory 212.

In diagnosis of an ophthalmologic disease such as glaucoma, there is a case that the retinal thickness is evaluated. In this case, measurement may be executed along three circular trajectories about the optic papilla center having radii m1, m2 and m3. For example, the radii m1, m2 and m3 are set to 1.2 mm, 1.6 mm and 2.0 mm, respectively.

In a case that such concentric trajectories are employed, the concentric trajectories are set in step S8, and a scan with a new signal light is executed based on the trajectories. Then, the image forming part 220 forms tomographic images along the three circular trajectories, respectively, and moreover, the image processor 230 measures the retinal thickness based on each of the tomographic images.

In a case that information of a normal range of the retinal thickness is stored in advance, the image processor 230 determines whether the measured retinal thickness is included in the normal range or not. The main controller 211 controls the display part 240 to display the result of this determination. Such a process relating to the retinal thickness is described in Japanese Patent Application 2007-45831, for example. This is the end of the description of the operation shown in FIG. 7.

Figure 8:
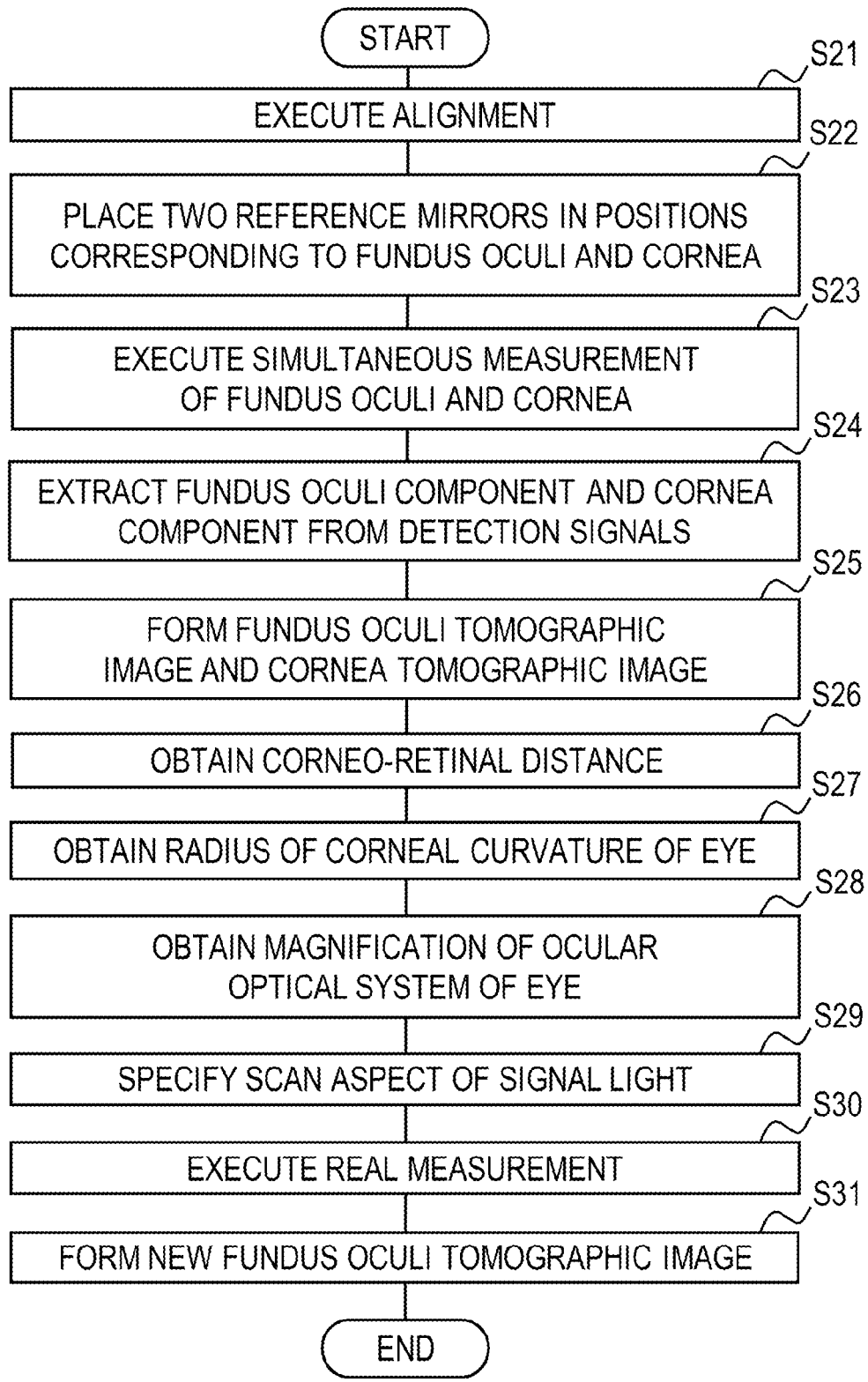
FIG. 8 is a flow chart showing an example of an operation of the embodiment of the optical image measuring device according to the present invention.

With reference to a flow chart shown in FIG. 8, an example of an operation of the optical image measuring device 1 will be described. In the operation example shown in FIG. 6, the standard value of the radius of corneal curvature is regarded as the radius of corneal curvature of the eye E to obtain the magnification of the ocular optical system. On the other hand, in the operation example shown in FIG. 8, the radius of corneal curvature of the eye E is obtained to calculate the magnification.

Firstly, in a like manner as in the operation example of FIG. 6, alignment of the optical system with respect to the eye E is executed (S21), the reference mirrors 174a and 174b are moved (S22), and the simultaneous measurement of the fundus oculi Ef and the cornea Ec is executed (S23). The interference component extracting part 221 extracts a fundus oculi component and a cornea component from the detection signals (S24). The image forming part 220 forms a fundus oculi tomographic image and a cornea tomographic image based on the extracted two signal components (S25).

The intraocular distance calculator 232 analyzes the fundus oculi tomographic image and the cornea tomographic image, and obtains a corneo-retinal distance of the eye E (S26).

Further, the corneal curvature calculator 235 obtains the radius of corneal curvature of the eye E based on the cornea tomographic image (S27). As mentioned before, the radius of corneal curvature may be obtained based on, instead of the cornea tomographic image, the position of the reference mirror 174b, namely, the optical path length of the second reference light LRb at the time of the simultaneous measurement.

The process in step S26 and the process in step S27 can be executed in any order. Alternatively, these processes can also be executed in parallel.

The magnification calculator 233 obtains the magnification of the ocular optical system of the eye E based on the corneo-retinal distance obtained in step S26, the radius of corneal curvature obtained in step S27 and the ocular optical information 212a (S28).

The scan aspect specifying part 234 specifies a scan aspect of the signal light LS to radiate the signal light LS to a predetermined position of the retina of the eye E, based on the magnification obtained in step S28 and the eye model (S29).

The main controller 211 controls to scan with the signal light LS based on the scan aspect specified in step S29 to execute real measurement (S30). The image forming part 220 forms a new tomographic image of the retina (the fundus oculi Ef) based on the detection signals obtained in the real measurement (S31). This is the end of the description of the operation shown in FIG. 8.

[Actions and Effects]

The actions and effects of the optical image measuring device 1 as described above will be described.

The optical image measuring device 1 acts in the following manner. Firstly, the optical image measuring device 1 splits the low-coherence light L0 into the signal light LS and the reference light LR, and splits the optical path of the reference light LR into two optical paths having different optical path lengths, thereby splitting the reference light LR into the two reference lights LRa and LRb.

Furthermore, the optical image measuring device 1 makes the reference lights LRa and LRb propagated through the two optical paths, respectively, interfere with the signal light LS propagated through the eye E, generates the interference light LC reflecting the morphology in each of two depth positions (the fundus oculi Ef and the cornea Ec) of the eye E, and detects the interference light LC to generate a detection signal. Then, the optical image measuring device 1 forms a fundus oculi tomographic image and a cornea tomographic image based on the detection signals, and analyzes these tomographic images to obtain a predetermined physical quantity (the corneo-retinal distance) of the eye E.

Since the optical image measuring device 1 that acts in this manner is capable of simultaneously executing measurement of two sites (the fundus oculi Ef and the cornea Ec) of the eye E, it is possible to measure, with high accuracy, the physical quantity of the eye E depicted in the tomographic images of the two sites.

Further, the optical image measuring device 1 acts so as to obtain the magnification of the ocular optical system of the eye E based on the corneo-retinal distance obtained as the predetermined physical quantity of the eye E. In this process, a standard value of the radius of corneal curvature and a measured value of the radius of corneal curvature of the eye E are used. Moreover, this process is executed based on an eye model formed based on the corneo-retinal distance and the ocular optical information 212a.

Further, the optical image measuring device 1 is provided with the scan unit 141 that scans a target position of the signal light LS on the eye E. Furthermore, the optical image measuring device 1 acts so as to, based on the abovementioned eye model and magnification, specify a scan aspect of the signal light to radiate the signal light to a predetermined position of the retina and scan with the signal light in accordance with the scan aspect to form a new fundus oculi tomographic image.

According to the optical image measuring device 1, it is possible to estimate the magnification of the ocular optical system of the eye E based on the fundus oculi tomographic image and cornea tomographic image having been acquired, and acquire a tomographic image in a predetermined position of the retina based on the estimated value and the eye model.

Furthermore, the optical image measuring device 1 is capable of obtaining the retinal thickness of the eye E based on the new tomographic image. Consequently, it is possible to measure the retinal thickness in a predetermined position of the retina, and it is possible to evaluate the retinal thickness with high accuracy, for example.

That is to say, it has been difficult up to now to accurately radiate the signal light to a predetermined position of the retina (for example, a circular trajectory that is centered on the optic papilla center and that has a predetermined radius) because of an influence of, for example, the magnification of the ocular optical system. On the other hand, according to this embodiment, it is possible to radiate the signal light to a target position with high accuracy based on the acquired magnification and the eye model, and consequently, it is possible to evaluate the retinal thickness with high accuracy.

MODIFIED EXAMPLE

The configuration described above is merely one example for favorably implementing the present invention. A person who intends to implement the present invention can properly make any modification within the scope of the present invention.

The predetermined physical quantity is not limited to the corneo-retinal distance. For example, it is possible to obtain the size (area, volume, and so on) of a lesion site as the predetermined physical quantity.

In the above embodiment, the predetermined physical quantity of the eye E is obtained by analyzing a plurality of tomographic images of the eye E. However, it is also possible to obtain the predetermined physical quantity by analyzing, instead of tomographic images, a detection signal from the CCD 184 and a signal obtained by processing the detection signal.

For example, by specifying the respective positions (the respective coordinate values) of the retinal surface and corneal front face based on a signal obtained by executing FFT on the fundus oculi component and the cornea component extracted from the detection signals, respectively, it is possible to obtain the corneo-retinal distance.

As far as tomographic images are formed from detection signals, the detection signals and the tomographic images can be identified with each other. Accordingly, "analyze a plurality of tomographic images and obtain a predetermined physical quantity of a measured object" in the present invention includes the process described in the modified example.

In the above embodiment, the optical path of the reference light LR is split into two, and two sites of the eye E are simultaneously measured. However, it is also possible to configure to split the optical path of the reference light into three or more and simultaneously measure three or more sites of a measured object.

Figure 9:
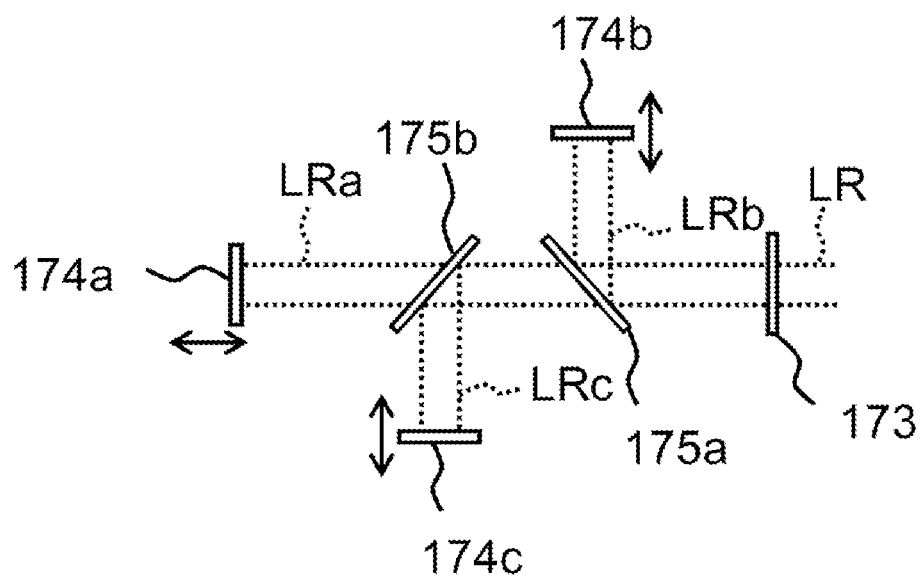
FIG. 9 is a schematic view showing an example of a configuration of an optical system of a modified example of the embodiment of the optical image measuring device according to the present invention.

A configuration example of an optical system that splits the optical path of the reference light LR into three is shown in FIG. 9. FIG. 9 shows a configuration in which part of the configuration shown in FIG. 4 is replaced. This "part" refers to a configuration including the density filter 173 and latter components on the optical path of the reference light LR.

In this configuration example, three reference mirrors 174a, 174b and 174c are formed. The reference mirrors 174a, 174b and 174c are moved by reference mirror drive mechanisms along directions of double-sided arrows shown in FIG. 9, respectively.

The reference light LR transmitted by the density filter 173 is split into two by a beam splitter 175a. The reflected light by the beam splitter 175a (the reference light LRb) is led to the reference mirror 174b.

The light transmitted by the beam splitter 175a is split into two by the beam splitter 175b. The reflected light by the beam splitter 175b (the reference light LRc) is led to the reference mirror 174c. The light transmitted by the beam splitter 175b (the reference light LRa) is led to the reference mirror 174a.

The reference lights LRa, LRb and LRc are reflected by the reference mirrors 174a, 174b and 174c, respectively. Then, the reference lights LRa, LRb and LRc are composed by the beam splitters 175a and 175b (also referred to as the reference light LR). This reference light LR is superposed on the signal light LS by the optical coupler 162 (refer to FIG. 4), and the interference light LC is generated.

This interference light LC includes information representing the morphologies of three sites of the eye E corresponding to the optical path lengths of the three optical paths.

The spectrometer 180 detects the spectral components of the interference light LC to generate detection signals. The image forming part 220 extracts three signal components from the detection signals, and forms tomographic images of the three sites of the eye E based on the respective components. The analysis processor 231 analyzes (at least two of) the three tomographic images based on the simultaneous measurement to obtain a predetermined physical quantity. In a case that the reference light LR is split into four or more, a similar process is executed.

The configuration for splitting the reference light is not limited to the configuration of the above embodiment, namely, the configuration using the beam splitter. For example, it is possible to split the reference light by using an optical member that extends the optical path length of part of the reference light.

Figure 10:
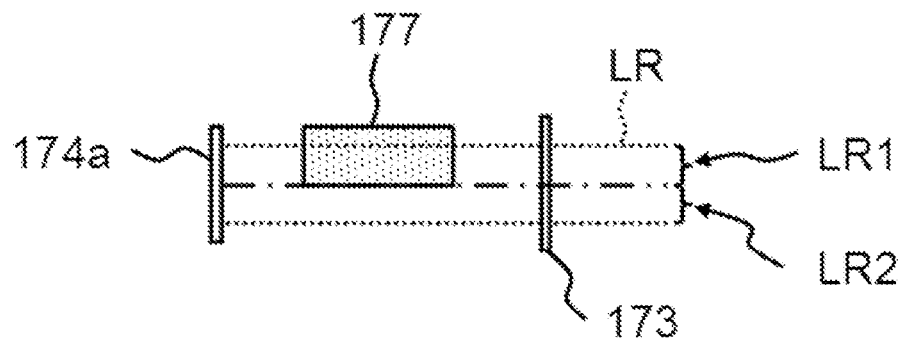
FIG. 10 is a schematic view showing an example of a configuration of an optical system of a modified example of the embodiment of the optical image measuring device according to the present invention.

An example of such a configuration is shown in FIG. 10. An optical member 177 is composed of a translucent (or transparent) material having a different refractive index from the atmosphere (air or the like) inside the OCT unit 150. The optical member 177 is composed of, for example, a glass block. The optical member 177 is placed in part of the optical path of the reference light LR, namely, in a position that transmits only a partial region of a beam cross-section of the reference light LR.

Part (reference light LR1) of the reference light LR that passes through the optical member 177 has a longer optical path length than part (reference light LR2) that does not pass through the optical member 177 because of an influence of the optical member 177.

With such a configuration, it is possible to simultaneously measure a plurality of (two) sites of the eye E.

It is also possible to execute simultaneous measurement of three or more sites of the eye E by forming a plurality of optical members having different extension distances of optical path length. Moreover, by selectively placing the plurality of optical members having different extension distances of optical path length on an optical path, it is possible to selectively execute simultaneous measurement of various depth positions of the eye E. Moreover, it is also possible to form an optical member that can continuously change the extension distance of optical path length.

In the above embodiment, the position of the reference mirror 174 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 1A and the OCT unit 150 with respect to the eye E to change the optical path length of the signal light LS. To be specific, for example, in a case that a measured object is not a living site, it is also effective to change the optical path length difference by moving the measured object in the depth direction.

The computer program used in the above embodiment can be stored in any kind of recording medium that can be read by a drive device of a computer. As this recording medium, for example, an optical disk, a magneto-optic disk (CD-ROM, DVD-RAM, DVD-ROM, MO, and so on), and a magnetic storing medium (a hard disk, a Floppy Disk™, ZIP, and so on) can be used. Moreover, it is possible to store into a storing device such as a hard disk drive and a memory.

Besides, it is possible to transmit/receive this program through a network such as the internet and a LAN.

The invention claimed is:

1. An optical image measuring device, comprising:
an optical system configured to split a light from a light source into a signal light and a reference light, split an optical path of the reference light into a plurality of optical paths having different optical path lengths to split the reference light into a plurality of reference lights including a first reference light having a first optical path length provided by a first reference mirror and a second reference light having a second optical path length provided by a second reference mirror, make the plurality of reference lights propagated through the plurality of optical paths, respectively, interfere with the signal light propagated through a measured object, and generate an interference light that reflects a morphology in each of a plurality of depth positions of the measured object;
a controller configured to displace positions of the first reference mirror and the second reference mirror so that an optical path length difference between the first optical path length and the second optical path length is equal to a standard value of the corneo-retinal distance; and
a detector configured to detect the generated interference light based on the control by the controller to generate a first detection signal based on the first reference light and a second detection signal based on the second reference light;
an image forming part configured to form a first tomographic image representing the morphology of the measured object in a first depth position based on the first detection signal and to form a second tomographic image representing the morphology of the measured object in a second depth position based on the second detection signal; and
an analyzer configured to analyze the first tomographic image to determine a retinal surface region of the measured object, to analyze the second tomographic image to determine a corneal surface region of the measured object and to obtain a distance between a point on the retinal surface region of the first tomographic image and a point on the corneal surface region of the second tomographic image.

2. The optical image measuring device according to claim 1, wherein:
the optical system includes a beam splitter configured to split the reference light having been split from the low-coherence light into the plurality of reference lights, and the reference mirrors placed on the respective optical paths of the plurality of reference lights;
the beam splitter is configured to compose the plurality of reference lights respectively reflected by the reference mirrors; and
the optical system is configured to make the plurality of reference lights having been composed interfere with the signal light to generate the interference light.

3. The optical image measuring device according to claim 1, wherein the optical system includes an optical member configured to extend the first optical path length of the first reference light having been split from the low-coherence light, and a first reference mirror configured to reflect the first reference light with the optical path extended by the optical member and the second reference light, the optical system being configured to make the first reference light reflected by the first reference mirror interfere with the signal light to generate the interference light.

4. The optical image measuring device according to claim 1, wherein:
the analyzer is configured to divide the standard value by a value of a refractive index of an ocular optical system included in ocular optical information stored in advance, and obtain the corneo-retinal distance based on the value of this quotient and the first and second tomographic images.

5. The optical image measuring device according to claim 1, wherein the analyzer includes a magnification calculator configured to obtain, as the predetermined physical quantity, a magnification of an ocular optical system of the living eye based on the obtained corneo-retinal distance.

6. The optical image measuring device according to claim 5, wherein: the magnification calculator is configured to obtain the magnification based on optical information of the ocular optical system included in ocular optical information stored in advance and the obtained corneo-retinal distance.

7. An optical image measuring device, according to claim 1, wherein:
the measured object is a living eye;
the first optical path length corresponding to a retina of the living eye, and the second optical path length corresponding to a cornea of the living eye;
the image forming part is configured to extract a first signal component corresponding to an interference component of the first reference light and the signal light reflected by the retina from the detection signal to form a first tomographic image showing a morphology of the retina as the one tomographic image, and extract a second signal component corresponding to an interference component of the second reference light and the signal light reflected by the cornea from the detection signal to form a second tomographic image showing a morphology of the cornea as the other tomographic image; and
the analyzer is configured to analyze the first tomographic image to identify a retinal surface of the living eye and to analyze the second tomographic image to identify a corneal surface of the living eye to obtain a cornea-retinal distance of the living eye.

8. The optical image measuring device according to claim 1, further comprising an alignment part configured to execute position matching of the optical system with respect to a living eye, wherein the analyzer is further configured to specify a position within a frame of the second tomographic image based on the interference light generated by the optical system after the position matching, and obtain a radius of corneal curvature of the living eye based on the specified position.

9. An optical image measuring device, comprising:
an optical system configured to split a light from a light source into a signal light and a reference light, split an optical path of the reference light into a plurality of optical paths having different optical path lengths to split the reference light into a plurality of reference lights, make the plurality of reference lights propagated through the plurality of optical paths, respectively, interfere with the signal light propagated through a measured object, and generate an interference light that reflects a morphology in each of a plurality of depth positions of the measured object;
a detector configured to detect the generated interference light to generate a detection signal;
an image forming part configured to form a plurality of tomographic images each representing the morphology of the measured object in a corresponding position among the plurality of depth positions based on the generated detection signal; and
an analyzer configured to analyze the plurality of tomographic images to obtain a distance between a position in one tomographic image of the plurality of tomographic images and a position in other tomographic image, wherein:
the measured object is a living eye;
the plurality of reference lights include a first reference light propagating on a first optical path having an optical path length corresponding to a retina of the living eye, and a second reference light propagating on a second optical path having an optical path length corresponding to a cornea of the living eye;
the image forming part is configured to extract a first signal component corresponding to an interference component of the first reference light and the signal light reflected by the retina from the detection signal to form a first tomographic image showing a morphology of the retina as the one tomographic image, and extract a second signal component corresponding to an interference component of the second reference light and the signal light reflected by the cornea from the detection signal to form a second tomographic image showing a morphology of the cornea as the other tomographic image; and
the analyzer is configured to analyze the first and second tomographic images to obtain a corneo-retinal distance of the living eye, wherein the analyzer includes a magnification calculator configured to obtain, as the predetermined physical quantity, a magnification of an ocular optical system of the living eye based on the obtained corneo-retinal distance, wherein: the magnification calculator is configured to obtain the magnification based on optical information of the ocular optical system included in ocular optical information stored in advance and the obtained corneo-retinal distance,
wherein: the ocular optical information includes a value of a radius of curvature of each of a back face and front face of the cornea, a value of a thickness of the cornea, a value of a refractive index of the cornea, a value of a radius of curvature of each of a back face and front face of a crystalline lens, a value of a thickness of the crystalline lens, a value of a refractive index of the crystalline lens, a value of a refractive index of a vitreous body, and a value of an anterior segment distance representing a distance between the front face of the cornea and the back face of the crystalline lens; and
the magnification calculator is configured to subtract the value of the anterior segment distance from the corneo-retinal distance to calculate a posterior segment distance representing a distance between the back face of the crystalline lens and the surface of the retina, form an eye model based on the ocular optical information and the posterior segment distance, and obtain the magnification based on the eye model.

10. The optical image measuring device according to claim 9, further comprising an alignment part configured to execute position matching of the optical system with respect to the living eye, wherein:
the analyzer includes a radius-of-corneal-curvature calculator configured to specify a position within a frame of the second tomographic image based on the interference light generated by the optical system after the position matching, and obtain a radius of corneal curvature of the living eye based on the specified position; and
the magnification calculator is configured to form the eye model based on the obtained radius of corneal curvature, instead of the value of the radius of corneal curvature included in the ocular optical system.

11. The optical image measuring device according to claim 9, further comprising an alignment part configured to execute position matching of the optical system with respect to the living eye, wherein:
the analyzer includes a radius-of-corneal-curvature calculator configured to obtain a radius of corneal curvature of the living eye based on the optical path length of the second optical path when the interference light is generated by the optical system after the position matching; and
the magnification calculator is configured to form the eye model based on the obtained radius of corneal curvature, instead of the value of the radius of corneal curvature included in the ocular optical system.

12. The optical image measuring device according to claim 9, wherein:
the optical system includes a scanner configured to scan a target position of the signal light on the living eye;
the analyzer includes a specifying part configured to, based on the eye model and the obtained magnification, specify a scan aspect of the signal light by the scanner to radiate the signal light to a predetermined position of the retina;
the optical system is configured to split a new low-coherence light into a signal light and a reference light and, while causing the scanner to scan with the new signal light based on the specified scan aspect, make the new reference light propagated on the first optical path interfere with the new signal light propagated through the retina to generate a new interference light;
the detector is configured to detect the new interference light to generate a new detection signal; and
the image forming part is configured to form a new tomographic image of the retina, based on the new detection signal.

13. The optical image measuring device according to claim 12, wherein the specifying part is configured to, by executing a ray tracing calculation based on the eye model and the obtained magnification, specify the scan aspect to radiate the signal light to the predetermined position of the retina of the eye model.

14. The optical image measuring device according to claim 12, wherein the specifying part is configured to specify the scan aspect for scanning the target position of the signal light along a circular trajectory that is centered on an optic papilla center of the retina and that has a predetermined radius.

15. The optical image measuring device according to claim 12, wherein the analyzer is configured to obtain a retinal thickness of the living eye based on the new tomographic image.

* * * * *